(12) United States Patent
Zapol et al.

(10) Patent No.: US 11,617,850 B2
(45) Date of Patent: Apr. 4, 2023

(54) DELIVERY SYSTEMS AND METHODS FOR ELECTRIC PLASMA SYNTHESIS OF NITRIC OXIDE

(71) Applicant: The General Hospital Corporation, Boston, MA (US)

(72) Inventors: Warren Zapol, Cambridge, MA (US); Aron Blaesi, Boston, MA (US); Binglan Yu, Quincy, MA (US); Matt Hickcox, Boston, MA (US)

(73) Assignee: The General Hospital Corporation, Boston, MA (US)

( * ) Notice: Subject to any disclaimer, the term of this patent is extended or adjusted under 35 U.S.C. 154(b) by 356 days.

(21) Appl. No.: 16/088,388

(22) PCT Filed: Mar. 27, 2017

(86) PCT No.: PCT/US2017/024331
§ 371 (c)(1),
(2) Date: Sep. 25, 2018

(87) PCT Pub. No.: WO2017/165888
PCT Pub. Date: Sep. 28, 2017

(65) Prior Publication Data
US 2020/0238041 A1 Jul. 30, 2020

Related U.S. Application Data

(60) Provisional application No. 62/313,529, filed on Mar. 25, 2016.

(51) Int. Cl.
*A61M 16/12* (2006.01)
*A61M 16/00* (2006.01)
(Continued)

(52) U.S. Cl.
CPC ........ *A61M 16/12* (2013.01); *A61M 16/0003* (2014.02); *A61M 16/022* (2017.08);
(Continued)

(58) Field of Classification Search
CPC ................ A61M 16/12; A61M 16/085; A61M 16/0858; A61M 16/1005; A61M 16/107;
(Continued)

(56) References Cited

U.S. PATENT DOCUMENTS 2,485,481 A 10/1949 Cotton
2,525,938 A 10/1950 Peck
(Continued)

FOREIGN PATENT DOCUMENTS

CN 1099997 A 3/1995
CN 1730115 A 2/2006
(Continued)

OTHER PUBLICATIONS

Gao et al. "Natural Convection at Microelectrodes". Analytical Chemistry (Year: 1995).*
(Continued)

*Primary Examiner* — Victoria Murphy
(74) *Attorney, Agent, or Firm* — Quarles & Brady LLP

(57) ABSTRACT

The present disclosure provides systems and method for electric plasma synthesis of nitric oxide. In particular, the present disclosure provides a nitric oxide (NO) generation system configured to produce a controllable output of therapeutic NO gas at the point of care.

32 Claims, 18 Drawing Sheets

(51) Int. Cl.
*A61M 16/08* (2006.01)
*A61M 16/10* (2006.01)
*B01J 19/08* (2006.01)
*C01B 21/32* (2006.01)

(52) U.S. Cl.
CPC ...... *A61M 16/085* (2014.02); *A61M 16/0858* (2014.02); *A61M 16/1005* (2014.02); *A61M 16/107* (2014.02); *B01J 19/088* (2013.01); *C01B 21/32* (2013.01); *A61M 2016/0024* (2013.01); *A61M 2016/0027* (2013.01); *A61M 2016/0036* (2013.01); *A61M 2016/102* (2013.01); *A61M 2016/103* (2013.01); *A61M 2016/1025* (2013.01); *A61M 2202/0216* (2013.01); *A61M 2202/0275* (2013.01); *A61M 2205/3368* (2013.01); *A61M 2205/3606* (2013.01); *B01J 2219/0809* (2013.01); *B01J 2219/0841* (2013.01); *B01J 2219/0875* (2013.01); *B01J 2219/0896* (2013.01)

(58) Field of Classification Search
CPC ........ A61M 16/022; A61M 2016/0024; A61M 2016/0027; A61M 2016/0036; A61M 2016/102; A61M 2202/0275; A61M 2205/3606; A61M 2016/1035; A61M 2250/00; A61M 16/0093; A61M 2202/0208; A61M 2202/0225; A61M 2202/0283; A61M 2205/3358; A61M 2230/00; A61M 2230/432; A61M 2230/435; A61M 2230/50; A61M 16/161; A61M 16/04; A61M 16/10; A61M 16/105; A61M 2016/0015; B01J 19/088; B01J 2219/0809; B01J 2219/0841; B01J 2219/0875; B01J 2219/0896; C01B 21/32; C01B 21/28; C01B 21/265
See application file for complete search history.

(56) References Cited

U.S. PATENT DOCUMENTS

| | | | |
|---|---|---|---|
| 2,684,448 A | 7/1954 | Nilles, Jr. | |
| 3,047,370 A | 7/1962 | Avtges et al. | |
| 3,225,309 A | 12/1965 | Phelps | |
| 4,287,040 A | 9/1981 | Alamaro | |
| 4,500,563 A | 2/1985 | Ellenberger et al. | |
| 4,505,795 A | 3/1985 | Alamaro | |
| 4,680,694 A | 7/1987 | Huynh et al. | |
| 4,695,358 A | 9/1987 | Mizuno et al. | |
| 4,705,670 A | 11/1987 | O'Hare | |
| 4,816,229 A | 3/1989 | Jensen et al. | |
| 4,877,589 A * | 10/1989 | O'Hare | B01J 12/002 422/186.24 |
| 5,285,372 A | 2/1994 | Huynh et al. | |
| 5,378,436 A | 1/1995 | Endoh et al. | |
| 5,396,882 A * | 3/1995 | Zapol | A61M 15/02 128/200.14 |
| 5,413,097 A | 5/1995 | Birenheide et al. | |
| 5,471,977 A | 12/1995 | Olsson et al. | |
| 5,485,827 A | 1/1996 | Zapol et al. | |
| 5,546,935 A | 8/1996 | Champeau | |
| 5,558,083 A | 9/1996 | Bathe et al. | |
| 5,573,733 A | 11/1996 | Salama | |
| 5,692,495 A | 12/1997 | Sheu | |
| 5,732,693 A | 3/1998 | Bathe et al. | |
| 5,752,504 A | 5/1998 | Bathe | |
| 5,839,433 A | 11/1998 | Higenbottam | |
| 5,845,633 A | 12/1998 | Psaros | |
| 6,000,397 A * | 12/1999 | Skog | A61M 16/085 128/204.22 |
| 6,089,229 A | 7/2000 | Bathe et al. | |
| 6,109,260 A | 8/2000 | Bathe | |
| 6,125,846 A | 10/2000 | Bathe et al. | |
| 6,164,276 A | 12/2000 | Bathe et al. | |
| 6,224,653 B1 | 5/2001 | Shvedchikov et al. | |
| 6,250,302 B1 | 6/2001 | Rantala | |
| 6,290,683 B1 * | 9/2001 | Erez | A61F 7/10 604/272 |
| 6,296,827 B1 | 10/2001 | Castor et al. | |
| 6,536,429 B1 | 3/2003 | Pavlov et al. | |
| 6,581,599 B1 | 6/2003 | Stenzler | |
| 6,668,828 B1 | 12/2003 | Figley et al. | |
| 6,758,214 B2 | 7/2004 | Fine et al. | |
| 6,920,876 B2 | 7/2005 | Miller et al. | |
| 6,955,171 B1 | 10/2005 | Figley et al. | |
| 6,955,790 B2 | 10/2005 | Castor et al. | |
| 6,986,351 B2 | 1/2006 | Figley et al. | |
| 7,025,869 B2 | 4/2006 | Fine et al. | |
| 7,040,313 B2 | 5/2006 | Fine et al. | |
| 7,122,018 B2 | 10/2006 | Stenzler et al. | |
| 7,220,393 B2 | 5/2007 | Miller et al. | |
| 7,255,105 B2 | 8/2007 | Figley et al. | |
| 7,299,785 B1 | 11/2007 | Lee | |
| 7,312,584 B2 | 12/2007 | Tamita et al. | |
| 7,335,181 B2 | 2/2008 | Miller et al. | |
| 7,485,324 B2 | 2/2009 | Miller et al. | |
| 7,498,000 B2 | 3/2009 | Pekshev et al. | |
| 7,516,742 B2 | 4/2009 | Stenzler et al. | |
| 7,520,866 B2 | 4/2009 | Stenzler et al. | |
| 7,531,133 B2 | 5/2009 | Hole et al. | |
| 7,560,076 B2 | 7/2009 | Rounbehler et al. | |
| 7,589,473 B2 | 9/2009 | Suslov | |
| 7,744,812 B2 | 6/2010 | Witherspoon et al. | |
| 7,861,717 B1 | 1/2011 | Krebs | |
| 7,955,294 B2 | 6/2011 | Stenzler et al. | |
| 3,030,849 A1 | 10/2011 | Suslov | |
| 8,043,252 B2 | 10/2011 | Miller et al. | |
| 8,079,998 B2 | 12/2011 | Hole et al. | |
| 8,151,791 B2 | 4/2012 | Arlow et al. | |
| 8,282,966 B2 | 10/2012 | Baldassarre et al. | |
| 8,291,904 B2 | 10/2012 | Bathe et al. | |
| 8,293,284 B2 | 10/2012 | Baldassarre et al. | |
| 8,344,627 B1 | 1/2013 | Hooke et al. | |
| 8,431,163 B2 | 4/2013 | Baldassarre et al. | |
| 8,518,457 B2 | 8/2013 | Miller et al. | |
| 8,573,209 B2 | 11/2013 | Bathe et al. | |
| 8,573,210 B2 | 11/2013 | Bathe et al. | |
| 8,574,531 B2 | 11/2013 | Miller et al. | |
| 8,717,733 B2 | 5/2014 | Getter et al. | |
| 8,776,794 B2 | 7/2014 | Bathe et al. | |
| 8,776,795 B2 | 7/2014 | Bathe et al. | |
| 8,790,715 B2 | 7/2014 | Montgomery et al. | |
| 8,795,222 B2 | 8/2014 | Stenzler et al. | |
| 8,795,741 B2 | 8/2014 | Baldassarre | |
| 8,821,828 B2 | 9/2014 | Hilbig et al. | |
| 8,846,112 B2 | 9/2014 | Baldassarre | |
| 9,067,788 B1 | 6/2015 | Spielman et al. | |
| 9,095,534 B2 | 8/2015 | Stenzler et al. | |
| 9,265,911 B2 | 2/2016 | Bathe et al. | |
| 9,279,794 B2 | 3/2016 | Tolmie et al. | |
| 9,295,802 B2 | 3/2016 | Bathe et al. | |
| 9,408,993 B2 | 8/2016 | Bathe et al. | |
| 9,573,110 B2 | 2/2017 | Montgomery et al. | |
| 9,770,570 B2 | 9/2017 | Schnitman et al. | |
| 9,795,756 B2 | 10/2017 | Flanagan et al. | |
| 9,982,354 B2 | 5/2018 | Kim | |
| 2001/0031230 A1 | 10/2001 | Castor et al. | |
| 2004/0019274 A1 | 1/2004 | Galloway, Jr. et al. | |
| 2004/0028753 A1 | 2/2004 | Hedenstierna et al. | |
| 2004/0031248 A1 | 2/2004 | Lindsey | |
| 2004/0181149 A1 | 9/2004 | Langlotz et al. | |
| 2005/0108813 A1 * | 5/2005 | Plut | A62D 5/00 2/458 |
| 2005/0172971 A1 | 8/2005 | Kolobow et al. | |
| 2005/0218007 A1 | 10/2005 | Pekshev et al. | |
| 2005/0263150 A1 | 12/2005 | Chathampally et al. | |
| 2005/0281465 A1 | 12/2005 | Marquart et al. | |
| 2006/0025700 A1 | 2/2006 | Fallik | |
| 2006/0172018 A1 | 8/2006 | Fine et al. | |
| 2006/0173396 A1 * | 8/2006 | Hatamian | A61M 1/369 604/6.13 |

(56) References Cited

U.S. PATENT DOCUMENTS

| | | |
|---|---|---|
| 2006/0276844 A1 | 12/2006 | Alon et al. |
| 2007/0151561 A1 | 7/2007 | Laurila |
| 2007/0190184 A1 | 8/2007 | Montgomery et al. |
| 2008/0017030 A1 | 1/2008 | Fleck |
| 2008/0078382 A1 | 4/2008 | LeMahieu et al. |
| 2008/0135044 A1 | 6/2008 | Freitag et al. |
| 2008/0202509 A1 | 8/2008 | Dillon et al. |
| 2010/0108493 A1 | 5/2010 | Wada et al. |
| 2010/0122705 A1* | 5/2010 | Moenning, Jr. ..... A61M 16/104 128/206.24 |
| 2010/0189808 A1 | 7/2010 | Gupta et al. |
| 2010/0245097 A1 | 9/2010 | Sung |
| 2010/0275911 A1 | 11/2010 | Arlow et al. |
| 2012/0037160 A1 | 2/2012 | Sung |
| 2012/0279500 A1 | 11/2012 | Singvogel et al. |
| 2012/0296265 A1 | 11/2012 | Dobrynin et al. |
| 2013/0123801 A1 | 5/2013 | Umasuthan et al. |
| 2013/0150863 A1 | 6/2013 | Baumgartner |
| 2014/0031668 A1 | 1/2014 | Mobasser et al. |
| 2014/0158121 A1 | 6/2014 | Flanagan et al. |
| 2014/0216452 A1 | 8/2014 | Miller et al. |
| 2014/0251787 A1* | 9/2014 | Montgomery ........... B01J 20/08 96/417 |
| 2014/0318537 A1* | 10/2014 | Bathe .................... A61M 16/04 128/203.14 |
| 2014/0363525 A1 | 12/2014 | Montgomery et al. |
| 2015/0000659 A1 | 1/2015 | Martin |
| 2015/0004248 A1 | 1/2015 | Morfill et al. |
| 2015/0034084 A1 | 2/2015 | Av-Gay et al. |
| 2015/0044305 A1 | 2/2015 | Av-Gay et al. |
| 2015/0072023 A1 | 3/2015 | Greenberg et al. |
| 2015/0090261 A1 | 4/2015 | Crosbie |
| 2015/0174158 A1 | 6/2015 | Av-Gay et al. |
| 2015/0272988 A1 | 10/2015 | Av-Gay et al. |
| 2016/0022731 A1 | 1/2016 | Av-Gay et al. |
| 2016/0030699 A1 | 2/2016 | Zapol et al. |
| 2016/0038710 A1 | 2/2016 | Zapol et al. |
| 2016/0183841 A1 | 6/2016 | Duindam et al. |
| 2016/0191887 A1 | 6/2016 | Casas |
| 2016/0228670 A1 | 8/2016 | Av-Gay et al. |
| 2016/0243328 A1 | 8/2016 | Tolmie et al. |
| 2016/0324580 A1 | 11/2016 | Esterberg |
| 2016/0367775 A1 | 12/2016 | Tolmie et al. |
| 2017/0014571 A1 | 1/2017 | Deem et al. |
| 2017/0014591 A1 | 1/2017 | Tolmie et al. |
| 2017/0014592 A1 | 1/2017 | Tolmie et al. |
| 2017/0021124 A1 | 1/2017 | Tolmie et al. |
| 2017/0065631 A1 | 3/2017 | Av-Gay et al. |
| 2017/0143758 A1 | 5/2017 | Greenberg et al. |
| 2017/0239289 A1 | 8/2017 | Av-Gay et al. |
| 2018/0049622 A1 | 2/2018 | Ryan et al. |
| 2018/0125883 A1 | 5/2018 | Av-Gay et al. |
| 2018/0133246 A1 | 5/2018 | Av-Gay et al. |

FOREIGN PATENT DOCUMENTS

| | | | |
|---|---|---|---|
| CN | 101828432 A | 9/2010 | |
| EP | 0621051 A2 | 10/1994 | |
| EP | 0763500 A2 | 3/1997 | |
| EP | 1036758 A1 | 9/2000 | |
| EP | 1854494 A1 | 11/2007 | |
| EP | 2151554 A1 | 2/2010 | |
| GB | 2277689 A * | 11/1994 | ........ A61M 16/1075 |
| JP | H04132560 A | 5/1992 | |
| JP | 2000102616 A | 4/2000 | |
| JP | 2001517108 A | 10/2001 | |
| JP | 2004065636 A | 3/2004 | |
| JP | 2006273677 A | 10/2006 | |
| JP | 2014179563 A | 9/2014 | |
| RU | 2199167 C1 | 2/2003 | |
| WO | 9507610 A1 | 3/1995 | |
| WO | 2004032719 A2 | 4/2004 | |
| WO | 2008112143 A1 | 9/2008 | |
| WO | 2011002606 A1 | 1/2011 | |
| WO | 2012094008 A1 | 7/2012 | |
| WO | 2012155213 A1 | 11/2012 | |
| WO | 2013052548 A2 | 4/2013 | |
| WO | 2013070712 A1 | 5/2013 | |
| WO | 2013181179 A1 | 12/2013 | |
| WO | 2014085719 A1 | 6/2014 | |
| WO | 2014143842 A1 | 9/2014 | |
| WO | 2014144151 A1 | 9/2014 | |
| WO | WO-2014144151 A1 * | 9/2014 | ............ A61M 15/02 |
| WO | 2015066278 A1 | 5/2015 | |
| WO | 2015127085 A1 | 8/2015 | |
| WO | 2016064863 A1 | 4/2016 | |

OTHER PUBLICATIONS

Keshav, Using Plasmas for High-Speed Flow Control and Combustion Control, Dissertation for Degree of Doctor of Philosophy, The Ohio State University, 2008, 268 pages.

Li, et al., Production of Medically Useful Nitric Monoxide Using AC Arc Discharge, Nitric Oxide, 2018, 73:89-95.

Mok, et al., Application of Positive Pulsed Corona Discharge to Removal of SO2 and NOx, Proceedings, ICESP VII, Sep. 20-25, 1998, Kyongju, Korea, 8 pages.

Namihira, et al., Production of Nitric Oxide Using a Pulsed Arc Discharge, IEEE Transactions on Plasma Science, 2002, 30(5):1993-1998.

PCT International Search Report, PCT/US2014/028439, dated Jul. 24, 2014.

PCT International Preliminary Report on Patentability, PCT/US2014/028439, dated Sep. 15, 2015.

PCT International Search Report, PCT/US2014/027986, dated Jul. 17, 2014.

PCT International Preliminary Report on Patentability, PCT/US2014/027986, dated Sep. 15, 2015.

PCT International Search Report and Written Opinion, PCT/US2015/056443, dated Jan. 6, 2016.

PCT International Search Report and Written Opinion, PCT/US2017/024331, dated Jun. 15, 2017.

Heli, Study on the Removal of Byproduct Nitrogen Dioxide from the Mixture of Inhaled Nitric Oxide Produced by Pulsed Arc Discharge, Thesis for Degree of Master of Engineering, Huazhong University of Science & Technology, China, Apr. 2006, 78 pages [Includes English Language Translation of Title Page and Abstract].

Hui, Research on the Production of Nitric Oxide by Pulsed Arc Discharge and the Curing of Respiratory Distress Instrument, Dissertation for Degree of Doctor of Philosophy in Engineering, Huazhong University of Science and Technology, China, Apr. 2005, 138 pages [Includes English Language Translation of Title Page and Abstract].

Kuo, Air Plasma for Medical Applications, Journal of Biomedical Science and Engineering, 2012, 5:481-495.

Namihira et al., Production of Nitric Monoxide Using Pulsed Discharges for a Medical Application, IEEE Transactions on Plasma Science, 2000, 28(1):109-114.

Hanning et al., Fortnightly Review—Pulse Oximetry: A Practical Review, BMJ, 1995, 311:367-370.

Encylopaedia Britannica, Inc., Definition of "Soda Lime", https://www.britannica.com/science/soda-lime, Nov. 12, 2018, 1 page.

Hui et al., The Effect of Flow Distribution on the Concentration of NO Produced by Pulsed Arc Discharge, Plasma Science and Technology, 2007, 9(6):766-769.

Intersurgical Complete Respiratory Systems, Carbon Dioxide Absorbents, Information Sheet, Issue 2 03.13, 8 pages.

Lorente, Chapter 20, Respiratory Filters and Ventilator-Associated Pneumonia: Composition, Efficacy Tests and Advantages and Disadvantages, In Humidification in the Intensive Care Unit, A.M. Esquinas (ed.), Springer-Verlag Berlin Heidelberg, 2012, pp. 171-177.

\* cited by examiner

| # | SPECIMEN | $^{193}$Ir (ng/g)* | $^{195}$Pt (ng/g)* |
|---|---|---|---|
| 1 | CONTROL | 6 | <DL |
| 2 | CONTROL | 4 | <DL |
| 3 | CONTROL | 2 | <DL |
| 4 | CONTROL | <DL | <DL |
| 5 | NO | <DL | <DL |
| 6 | NO | 4 | <DL |
| 7 | NO | <DL | <DL |
| 8 | NO | 2 | <DL |
| 9 | CONTROL | <DL | <DL |
| 10 | CONTROL | <DL | <DL |
| 11 | CONTROL | 1 | <DL |
| 12 | CONTROL | <DL | <DL |
| 13 | NO | <DL | <DL |
| 14 | NO | <DL | <DL |
| 15 | NO | <DL | <DL |
| 16 | NO | 3 | 1 |

FIG. 20

DELIVERY SYSTEMS AND METHODS FOR ELECTRIC PLASMA SYNTHESIS OF NITRIC OXIDE

CROSS-REFERENCE TO RELATED APPLICATIONS

The present application is a U.S. National Phase of PCT Application No. PCT/US2017/024331 filed on Mar. 27, 2017, which is based on, claims priority to, and incorporates herein by reference in its entirety, U.S. Provisional Patent Application No. 62/313,529, filed on Mar. 25, 2016, and entitled "Delivery Systems and Methods for Electric Plasma Synthesis of Nitric Oxide."

STATEMENT REGARDING FEDERALLY SPONSORED RESEARCH

Not Applicable.

BACKGROUND

The disclosure relates generally to the electrical plasma synthesis of nitric oxide (NO) from gases and, more specifically, to systems and methods for delivering NO to be used in medical applications.

NO is a crucial mediator of many biological systems, and is known to control the level of systemic and pulmonary artery blood pressure, help the immune system kill invading parasites that enter cells, inhibit the division of cancer cells, transmit signals between brain cells, and contribute to the death of brain cells that debilitates people with strokes or heart attacks, among other things. NO mediates the relaxation of smooth muscle present, for example, in the walls of blood vessels, bronchi, the gastrointestinal tract, and urogenital tract. Administration of NO gas to the lung by inhalation has been shown to produce localized smooth muscle relaxation within the lung's blood vessels and is widely used to treat pulmonary hypertension, pneumonia, hypoxemic respiratory failure of a newborn, etc. without producing systemic side effects such as systemic hypotension.

Inhaling NO can immediately produce potent and selective pulmonary vasodilation that improves the matching of ventilation with perfusion, thereby increasing an injured lung's oxygen transport efficiency, and breathing NO can raise the arterial oxygen tension. Breathing NO produces the rapid onset of pulmonary vasodilator action occurring within seconds of commencing breathing with the absence of systemic vasodilatation. Once inhaled, NO diffuses through the pulmonary vasculature into the bloodstream, where it is rapidly inactivated by combination with oxyhemoglobin (the NO dioxygenation reaction). Therefore, the vasodilatory effects of inhaled NO are limited to the lung in the treatment of acute and chronic pulmonary hypertension. Inhaled NO can also be used to prevent ischemia reperfusion injury after percutaneous coronary intervention in adults with heart attacks. Furthermore, inhaled NO can produce systemic anti-inflammatory and anti-platelet effects by increasing the levels of circulating NO biometabolites (including cyclic guanosine monophosphate) and by other mechanisms, such as the oxidation of circulating ferrous hemoglobin to methemoglobin in the plasma. Further still, NO has known anti-microbial activity.

BRIEF SUMMARY

The present disclosure provides systems and method for electric plasma synthesis of nitric oxide. In particular, the present disclosure provides a nitric oxide (NO) generation system configured to produce a controllable output of therapeutic NO gas at the point of care.

In one aspect, the present disclosure provides an apparatus for generating nitric oxide including a housing having a first wall with an aperture formed therein to provide access to a recess and a second wall permitting gas flow therethrough, an insulator arranged in the recess, and a pair of electrodes arranged within the housing to at least partially engage the insulator. The apparatus further includes a power supply connected to the pair of electrodes to energize the pair of electrodes to induce a chemical reaction within the recess that generates nitric oxide, a particle filter arranged to filter particulates about the second wall, and a scavenger arranged proximate to the particle filter to control an amount of undesired byproducts from the chemical reaction induced by operation of the pair of electrodes. The apparatus further includes a controller in communication with the power supply and configured to selectively energize the pair of electrodes to achieve one or more electric discharges between the electrodes to generate the nitric oxide within the housing, and a flow path configured to non-mechanically direct the nitric oxide through the second wall of the housing and into an airway of a subject using the apparatus.

In one aspect, the present disclosure provides an apparatus for generating nitric oxide including a housing having a first wall with an aperture formed therein to provide access to a recess and a second wall permitting gas flow therethrough, an insulator arranged in the recess, and a reaction chamber defined by a volume between the housing and the insulator. The apparatus further includes a pair of electrodes arranged within the housing to at least partially engage the insulator, a power supply connected to the pair of electrodes to energize the pair of electrodes to induce a chemical reaction within the reaction chamber that generates nitric oxide, a particle filter arranged to filter particulates about the second wall, and a scavenger arranged proximate to the particle filter to control an amount of undesired byproducts from the chemical reaction induced by operation of the pair of electrodes. The apparatus further includes a controller in communication with the power supply and configured to selectively energize the pair of electrodes to achieve one or more electric discharges between the pair of electrodes to generate the nitric oxide within the reaction chamber. The second wall is dimensioned to engage a breathing tube coupled to an airway of a subject using the apparatus and the reaction chamber is dimensioned to direct the nitric oxide through the second wall and into the breathing tube coupled to the airway of the subject.

In yet another aspect, the present disclosure provides an apparatus for generating nitric oxide to be coupled to a breathing tube connected to an airway of a subject. The apparatus includes a housing having a first wall having an aperture formed therein to provide access to a recess and a second wall permitting gas flow therethrough and in fluid communication with the breathing tube, an insulator arranged in the recess, and a pair of electrodes arranged within the housing to at least partially engage the insulator. The apparatus further includes a power supply connected to the pair of electrodes to energize the pair of electrodes to induce a chemical reaction within the recess that generates nitric oxide, a particle filter arranged to filter particulates about the second wall, and a scavenger arranged proximate to the particle filter to control an amount of undesired byproducts from the chemical reaction induced by operation of the pair of electrodes. The apparatus further includes one or more gas sensors arranged between the airway of the patient and the pair of electrodes to measure at least one of a nitric oxide concentration, a nitrogen dioxide concentration, an oxygen concentration, and a carbon dioxide concentration, a flow meter configured to measure a flow rate within the breathing tube, a controller in communication with the power supply, the one or more gas sensors, and the flow meter and configured to selectively energize the pair of electrodes to achieve one or more electric discharges between the pair of electrodes to generate nitric oxide within the housing, and a flow path configured to non-mechanically direct the nitric oxide through the second wall of the housing and into the breathing tube.

In still another aspect, the present disclosure provides a method for generating nitric oxide in a breathing tube coupled to an airway of a subject. The method includes engaging a nitric oxide generator with the breathing tube such that fluid communication is provided between the nitric oxide generator and the breathing tube, triggering the nitric oxide generator to produce a desired concentration of nitric oxide gas, and determining output parameters sent to a pair of electrodes arranged within the nitric oxide generator such that a desired amount of nitric oxide gas is generated. The method further includes upon determining the output parameters, supplying the output parameters the pair of electrodes to generate the desired amount of nitric oxide gas, and non-mechanically directing the generated nitric oxide gas out of the nitric oxide generator and into the breathing tube.

The foregoing and other aspects and advantages of the invention will appear from the following description. In the description, reference is made to the accompanying drawings which form a part hereof, and in which there is shown by way of illustration a preferred embodiment of the invention. Such embodiment does not necessarily represent the full scope of the invention, however, and reference is made therefore to the claims and herein for interpreting the scope of the invention.

BRIEF DESCRIPTION OF DRAWINGS

The invention will be better understood and features, aspects and advantages other than those set forth above will become apparent when consideration is given to the following detailed description thereof. Such detailed description makes reference to the following drawings.

FIG. 20 shows a table illustrating iridium and platinum high resolution inductive coupled plasma mass spectrometer analysis of murine lung specimens for a number of different mice assayed after the twenty eight day breathing test. DL is the detectable level limit.

DETAILED DESCRIPTION

The use of the terms "downstream" and "upstream" herein are terms that indicate direction relative to the flow of a gas. The term "downstream" corresponds to the direction of gas flow, while the term "upstream" refers to the direction opposite or against the direction of gas flow.

Currently, administration of inhaled nitric oxide (NO) therapy requires the use of heavy compressed gas cylinders, a gas cylinder distribution network, a complex delivery device, gas monitoring and calibration devices, and trained respiratory therapy staff. These requirements for administering NO therapy present a significant cost to the institution (e.g., a hospital) administering the NO therapy and, therefore, to the patient receiving the NO therapy. For many institutions, inhaled NO therapy can be one of the most expensive drugs used in neonatal medicine. The use of bulky gas cylinders and the expense of inhaled NO therapy result in inhaled NO therapy not being available in most of the world and it is not available for outpatient use.

Several methods have been attempted to produce NO for biomedical purposes, such as, chemically preparing NO from $N_2O_4$ requiring extensive scavenging with antioxidants. Various electrical systems have also been attempted, such as, pulsed arc, gliding arc, dielectric barrier, microwave, corona, radio frequency induced coupled discharge, and non-thermal atmospheric pressure high-frequency plasma discharge. However, these systems and methods produce large amounts of harmful byproducts (e.g., nitrogen dioxide ($NO_2$) and ozone ($O_3$)) and require complex purification systems. Additionally, these electrical systems can be required, when coupled to a ventilator, to supply the ventilator bias flow which can be up to 30-80 liters per minute. Such a large flow demand requires the current electrical systems to generate a large amount of wasted NO gas (i.e., NO that is not inhaled by the patient and, thus, wasted).

Due to the current difficulties in administering and generating NO for inhalation therapy, it would be desirable to have a simplified NO generation system that is dimensioned to be placed directly in the inhalation pathway by coupling an NO generator directly to a breathing tube (e.g., an endotracheal tube, a tracheostomy tube, etc). In one non-limiting example, the NO generator is coupled to an exit of the breathing tube (i.e., the distal end of the breathing tube positioned outside of the patient). In this position, there is no requirement to supply bias flow which considerably reduces the NO generation requirements which thereby enables the NO generator to be smaller in size, require less power, and generate less heat during operation.

Figure 1:
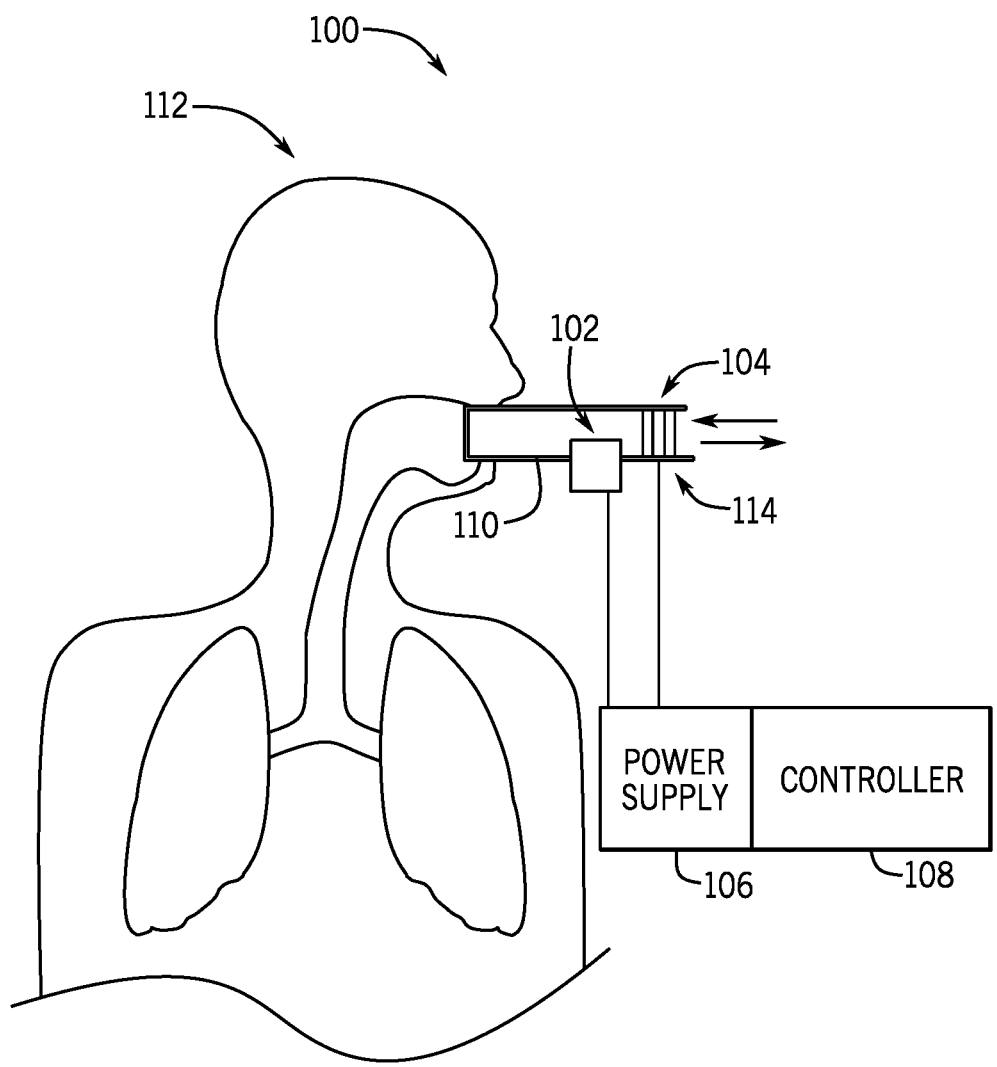
FIG. 1 shows a schematic illustration of a nitric oxide generation system according to one aspect of the present disclosure.

FIG. 1 shows one non-limiting example of a NO generation system 100 according to one aspect of the present disclosure. The NO generation system 100 includes an NO generator 102, a flow meter 104, a power supply 106, and a controller 108. The NO generator 102 is coupled to a breathing tube 110 placed in the airway or trachea of a patient 112. The patient 112, as illustrated may be a human. However, the system 100 may be used with any of a variety of subjects, which may include a human, other mammal, or other animal, or may be used in other applications that do not include a subject. That is, the NO generator 102 is coupled to the breathing tube 110 such that NO gas is produced by the NO generator 102 at, or in, or next to, the breathing tube 110. The illustrated breathing tube 110 is in the form of an endotracheal tube. It should be appreciated that, in other non-limiting examples, the breathing tube 110 may be in the form of any tube placed in the airway of the patient 112, for example, a tracheostomy tube. The NO generator 102 is coupled to a distal end 114 (i.e., the end of the breathing tube 110 positioned outside of the patient 112) of the breathing tube 110.

The NO generator 102 is configured to produce NO gas by electric discharge, as will be described in detail below. The concentration of NO gas, $C_{NO}$, delivered by the NO generator 102 to the patient 112 can be defined as:

$$C_{NO} = \frac{dNO}{dt}\frac{1}{Q} \quad (1)$$

where dNO/dt is the NO gas generation rate and Q is a gas flow rate. By Equation 1, the NO gas concentration delivered to the patient 112 can be defined when the NO gas concentration rate is controlled (by proper control of the NO generator 102 by the controller 108) and the gas flow rate is measured by the flow meter 104. Thus, an exemplary NO generator 102 is to be structured to produce NO gas at, or in, the breathing tube 110 and configured to produce a controllable output of NO gas.

Figure 2:
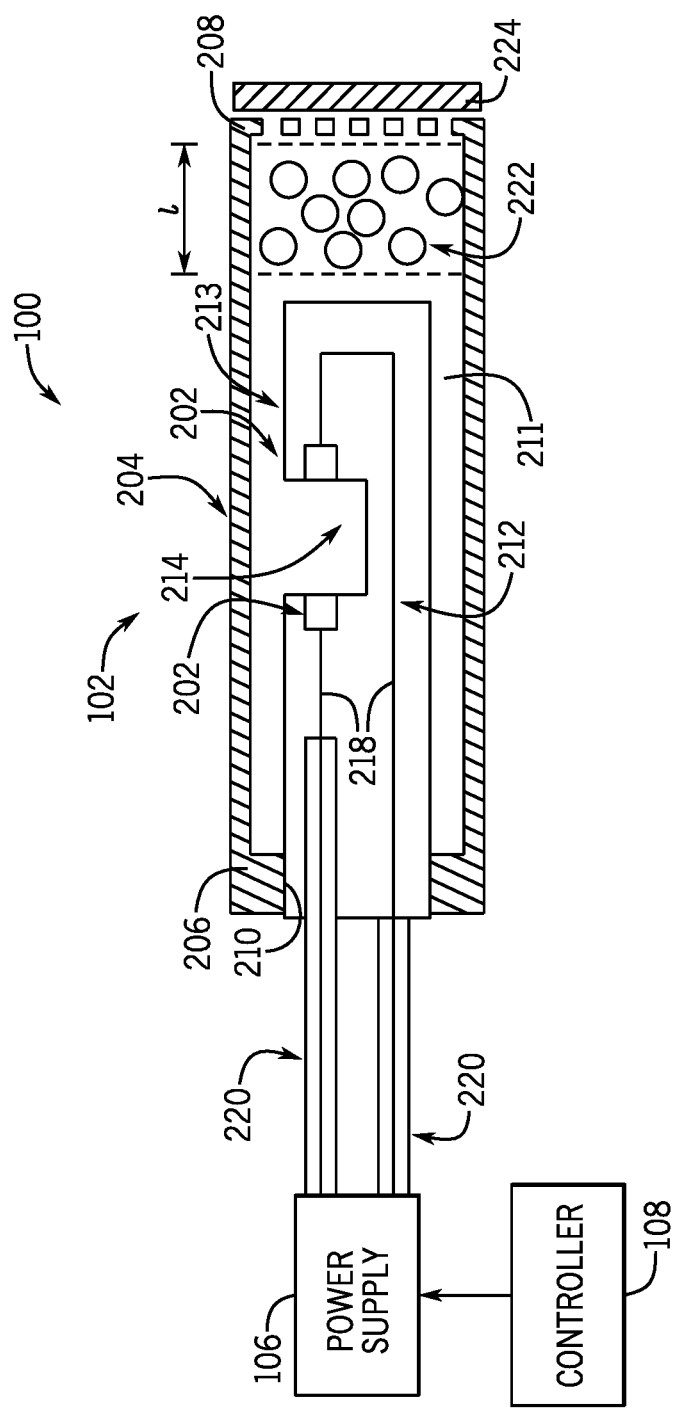
FIG. 2 shows a detailed schematic of a nitric oxide generator of a nitric oxide generation system according to one aspect of the present disclosure.

FIG. 2 shows one non-limiting example of an exemplary NO generator 102. As shown in FIG. 2, the NO generator 102 includes a pair of opposing electrodes 202 arranged within a housing 204. The electrodes 202 can be fabricated from or plated with tungsten carbide, carbon, nickel, iridium, titanium, platinum, rhenium, or an alloy of the aforementioned materials. In one non-limiting example, the electrodes 202 are fabricated from or plated with iridium due to a lower ratio of $NO_2$ to NO generated by iridium when compared to other metals, as described in International Patent Application No. PCT/US2015/056443 ('443 International Application) which is hereby incorporated herein by reference. In other non-limiting examples, the NO generator 102 may include two or more pairs of electrodes 202. The electrodes 202 are configured to create a plasma there between upon electric discharge. The plasma generated by the electrodes 202 generates NO gas, as long as nitrogen and oxygen are present in the atmosphere in which the NO generator 102 is placed.

The housing 204 may be fabricated from a thermal and electrical insulating material. In some non-limiting examples, the housing 204 can be fabricated from a plastic material, for example, polytetrafluoroethylene (PTFE). The housing 204 includes a first wall 206 and a second wall 208 opposing the first wall 206. The first wall 206 includes an aperture 210 that provides access to a recess 211 formed by an interior of the housing 204. The aperture 210 may be dimensioned to receive an insulator 212 to form a reaction chamber 213 between the insulator 212 and the housing 204. That is, the reaction chamber 213 is defined by the volume between the housing 204 and the insulator 212. The second wall 208 may be perforated to enable gas flow therethrough. A flow path can be defined along the reaction chamber 213 and through the second wall 208. The flow path can be configured to direct NO generated by the NO generator 102, as will be described below.

The housing 204 is configured to prevent sputum, pulmonary edema fluid, and the like from reaching the electrodes 202 but allow NO gas to flow through the second wall 208. In another non-limiting example, a lumen scraper may be coupled to the housing 204 to remove mucus.

The insulator 212 may be fabricated from an electrical insulating material that can sustain high temperatures generated during discharge of the electrodes 202. In one non-limiting example, the insulator 212 may be fabricated from a ceramic material. As shown in FIG. 2, the electrodes 202 are secured within the insulator 212. The insulator 212 defines an electrode gap 214 dimensioned to place the electrodes 202 a pre-defined distance from each other. A pair of high voltage wires 218 extend through the insulator 212 and connect the electrodes 202 to the power supply 106. The high voltage wires 218 may include wire insulation 220 except when located within the insulator 212, which acts to electrically insulate and prevent shorting.

A scavenger 222 may be arranged downstream of the electrodes 202 within the housing 204. As shown in FIG. 2, the scavenger 222 may be arranged adjacent to the second wall 208. The scavenger 222 may be configured to control undesirable byproducts (e.g., $NO_2$ and $O_3$) produced by the system 100. In one non-limiting example, the scavenger 222 may be fabricated from calcium hydroxide ($Ca(OH)_2$). In another non-limiting example, the scavenger 222 may be a reductant scavenger composed of any reductant (e.g., ascorbic acid).

A concentration of $NO_2$, $C_{NO2}$, downstream of the scavenger 222 can be approximated as:

$$C_{NO2} \sim C_{NO2,0} \exp\left(-\frac{D_{NO2}}{H^2 \cdot v_{gas}} l\right) \quad (2)$$

where $C_{NO2,0}$ is the concentration of $NO_2$ upstream of the scavenger 222, $D_{NO2}$ is the diffusivity of $NO_2$ in air, H is a height between adjacent particles of the scavenger 222, $v_{gas}$ is a velocity of the gas flowing into the scavenger 222, and l is a length defined by the scavenger 222. Solving Equation 2 for l enables a minimum length l of the scavenger 222 to be approximated for a range of operating conditions. In most non-limiting examples, a minimum length l of the scavenger 222 can be approximately one millimeter. Thus, the size of the scavenger 222 does not restrict the overall size of the NO generator 102. A size of the perforations defined by the second wall 208 of the housing 204 are dimensioned to ensure that the contents of the scavenger 222 do not escape from within the housing 204.

The NO generator 102 includes a particle filter 224 arranged downstream of the scavenger 222. The particle filter 224 may be configured to filter particles prior to the gas entering the airway of a patient. For example, the particle filter 224 can prevent fragments from the scavenger 222 and/or particles/vapors that boil off from the electrodes 202 due to the high temperatures generated during discharge from entering the airway of a patient. In one non-limiting example, the particle filter 224 can be configured to filter particles with a diameter larger than approximately 0.22 micrometers (μm). In one configuration, the particle filter 224 may be a high efficiency particulate absorption (HEPA) filter. As described in the '443 International Application, a 0.22 um particle filter arranged upstream of the patient is sufficient to remove electrode fragments that erode and vaporize during operation. It should be known that the particle size filtered by the particle filter 224 is not meant to be limiting in any way, and alternative particle filters that filter different particle sizes are within the scope of the present disclosure. However, the particle size filtered by the particle filter 224 should be sufficiently small to maintain the safety and health of a patient.

The illustrated particle filter 224 may be arranged outside of the housing 204 and downstream of the scavenger 224. In another non-limiting example, the particle filter 224 can be integrated into the housing 204 and arranged between the scavenger 222 and the second wall 208 of the housing 204.

With continued reference to FIG. 2, the power supply 106 may be configured to energize the electrodes 202 (e.g., by supplying a discharge voltage across) to induce a chemical reaction. Once the electrodes 202 are energized by the power supply 106, an electric plasma discharge occurs between the electrodes 202 that generates NO gas in the presence of nitrogen and oxygen. In one non-limiting example, the power supply 106 can be a resonant high voltage power supply. The use of a resonant high voltage power supply may enable the NO generation system 100 to produce more NO gas per watt of power when compared to simple capacitor and coil discharge designs. In another non-limiting example, the power supply 106 can be a synchronous power supply configured to adjust for variations in the load.

The power supply 106 may be in communication with the controller 108. The controller 108 may be configured to selectively instruct the power supply 106 to supply the discharge voltage across the electrodes 202 thereby producing NO gas. This is accomplished by the controller 108 supplying an electrical signal to the power supply 106. The electrical signal supplied by the controller 108 may be configured to control, for example, an electrical discharge frequency (i.e., a frequency of the electric plasma discharges between the electrodes 202) and/or a discharge duration (i.e., a length of time that each electric plasma discharge lasts between the electrodes 202). In some exemplary non-limiting examples, the controller 108 can be configured to supply an electrical signal to the power supply 106 such that the electrical discharge frequency may be between approximately 1 kHz and approximately 1 MHz, and the discharge duration may be between approximately 0.1 microsecond (μs) an approximately 100 μs.

Figure 3:
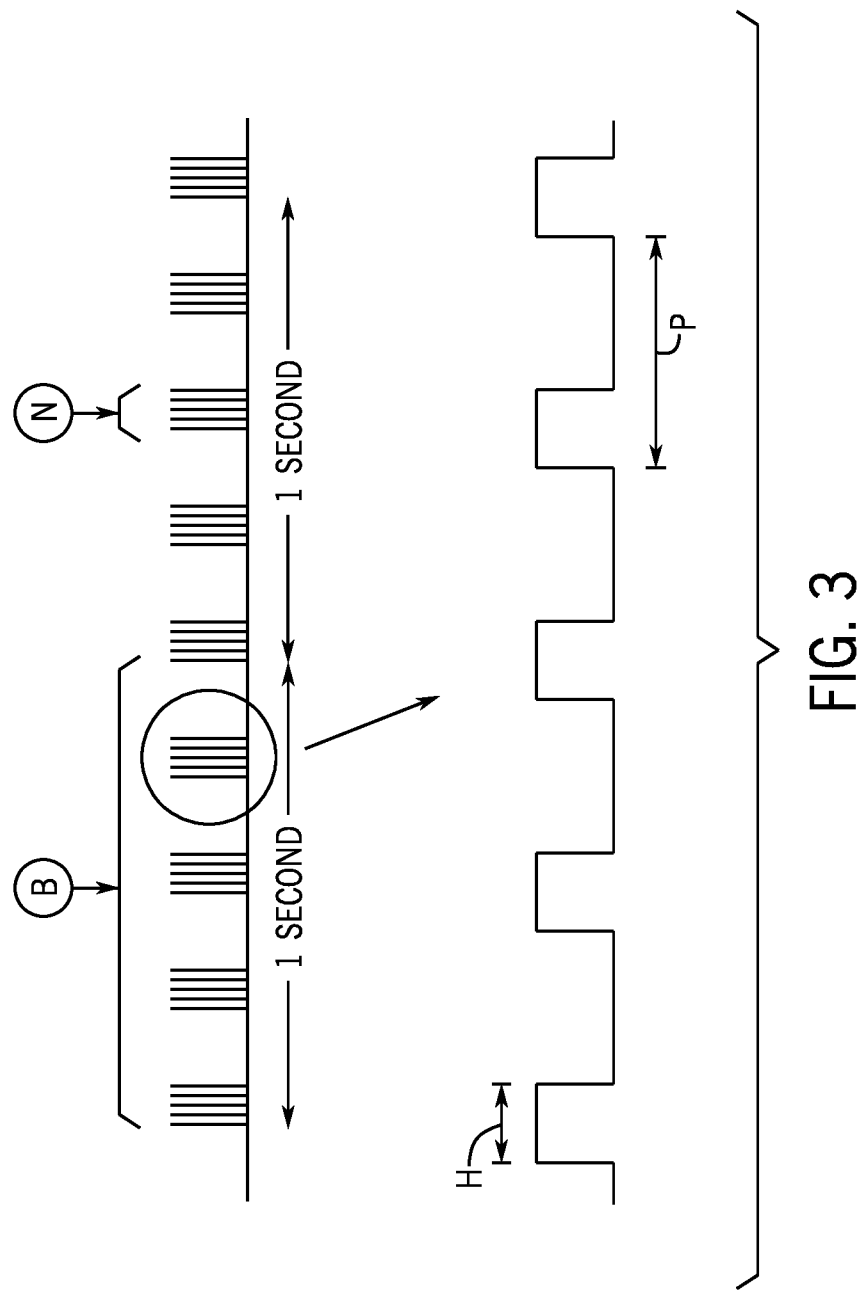
FIG. 3 shows an electrical signal that may be applied to electrodes of the nitric oxide generator of FIG. 2 according to one aspect of the present disclosure.

FIG. 3 shows one non-limiting example of an electrical signal supplied to the electrodes 202 by the controller 108. As shown in FIG. 3, the electrical signal can include groups of square waves where each individual square wave in the respective group represents a discharge of the electrodes 202. In this non-limiting example, the controller 108 can be configured to control a number spark groups per second (B), a number of individual sparks per group (N), a time between individual sparks (P), and a pulse duration of each individual square wave in the group (H). Varying the values of B, N, P, and H can alter concentrations of NO and $NO_2$ generated by the NO generator 102. In one configuration, the controller 108 can include a theoretical model for generating a given concentration of NO gas based on the values of B, N, P, and H. Thus, the controller 108 may be configured to supply an electric signal to the power supply 106 that produces a desired concentration of NO gas.

Figure 4:
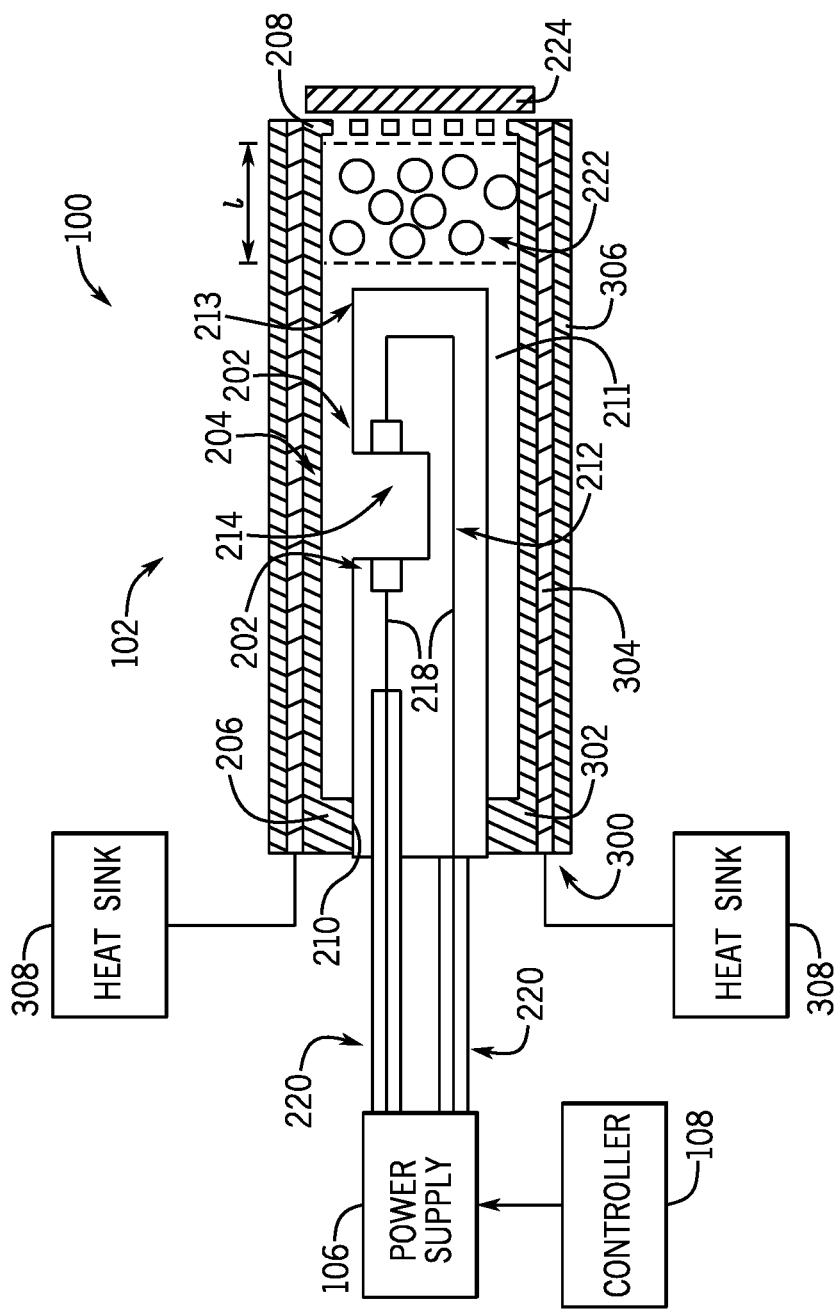
FIG. 4 shows a detailed schematic of the nitric oxide generator of FIG. 2 with a layered housing according to another aspect of the present disclosure.

Turning to FIG. 4, in another non-limiting example, the housing 204 of the NO generator 102 includes a plurality of layers 300. The illustrated plurality of layers 300 comprise a first layer 302, a second layer 304, and a third layer 306. The second layer 304 may be arranged between the first layer 302 and the third layer 306 and may be connected to a heat sink 308. The first layer 302 and the third layer 306 are both fabricated from an electrical insulating material with a low thermal conductivity (e.g., PTFE). The second layer 304 may be fabricated from a material with a high thermal conductivity (e.g., aluminum, copper, etc.). The high thermal conductivity of the second layer 304 provides efficient dissipation of heat generated by the electric discharge of the electrodes 202 to the heat sink 308. The heat dissipation provided by the housing 204 can lower an operating temperature of the NO generator 102 to safe levels for placement at, or in, a breathing tube (i.e., at the point of care).

Figure 5:
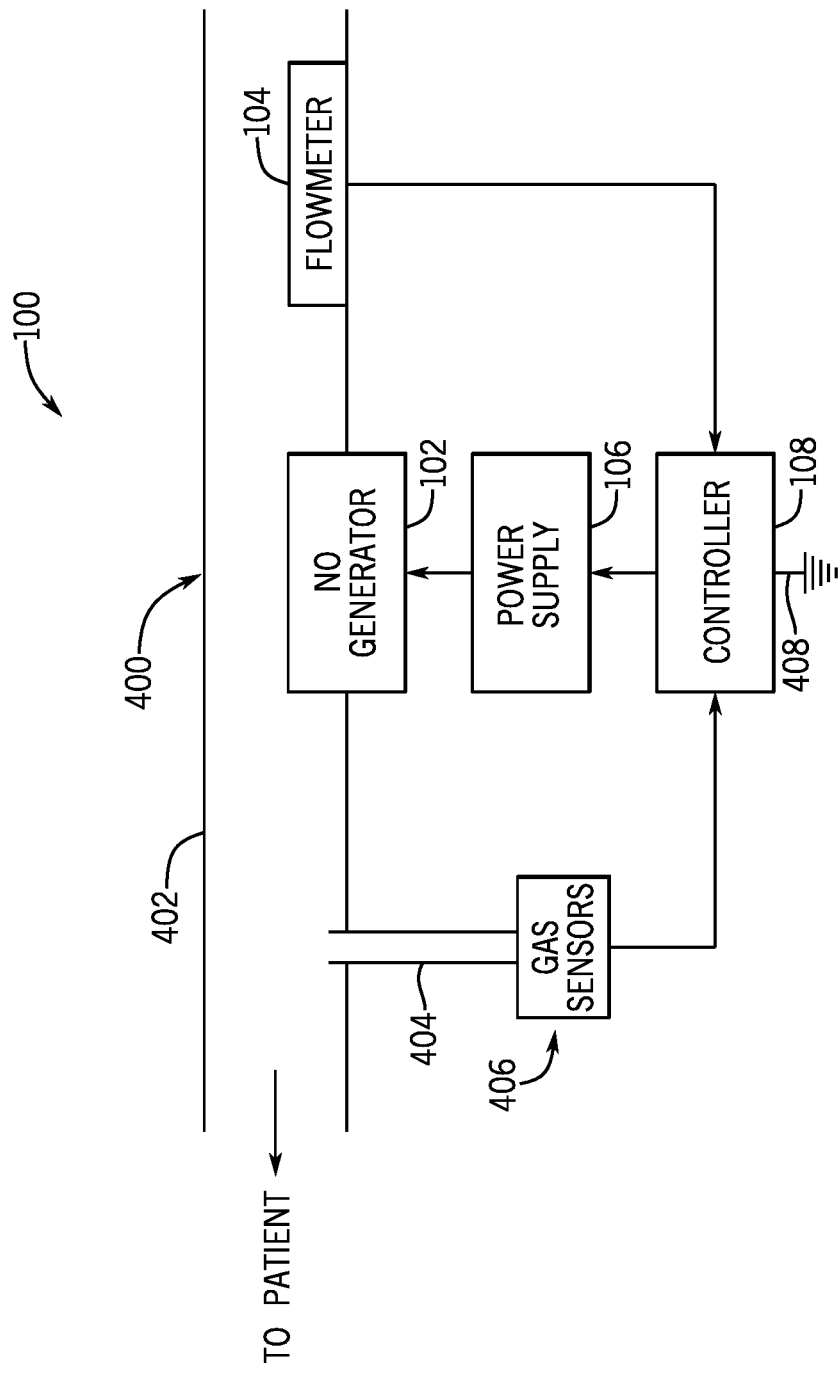
FIG. 5 shows a detailed schematic of a nitric oxide generation system including the nitric oxide generator of FIG. 2 coupled to a breathing tube according to one aspect of the present disclosure.

As described above, in operation, the NO generation system 100 can be installed at, or in, a breathing tube providing access to an airway of a patient. FIG. 5 shows one non-limiting example implementation of the NO generation system 100. As shown in FIG. 5, the NO generator 102 may be placed at a distal end 400, or exit, of a breathing tube 402 such that NO gas generated by the NO generator 102 flows into the breathing tube 402 and then into an airway of a patient. Preferably, the NO generator 102 may be arranged such that the second wall 208 is at, or in, the distal end 400 of the breathing tube 402 thereby providing fluid communication between the NO generator 102 and an airway of a patient. The breathing tube 402 may be an endotracheal tube, a tracheostomy tube, or any other medical tube or mask or nasal airway configured to provide access to an airway of a patient. The breathing tube 402 can be used for spontaneous ventilation or positive end expiratory pressure system or can be coupled, for example, to a ventilator or another mechanically assisted breathing device.

A sample line 404 may be arranged between the NO generator 102 and the patient, and provides fluid communication between the output of the NO generator 102 and one or more gas sensors 406. The one or more gas sensors 406 are configured to measure a concentration of one or more gas species. For example, the one or more gas sensors 406 can include an NO sensor, an $NO_2$ sensor, an $O_2$ sensor, and a $CO_2$ sensor. It can also comprise a barometric pressure indicator for altitude correction of gas pressures. Alternatively or additionally, the one or more sensors 406 may include one or more of a pressure sensor, a temperature sensor, and a humidity sensor. The one or more gas sensors 406 are in communication with the controller 108 to provide feedback of the output characteristics of the NO generator 102 to the controller 108. Since the NO output may be maximal at approximately 50% oxygen and reduced with either more or less oxygen in the mixture, the oxygen level measurement can be important to compute the energy given to the plasma by the electrodes 202 to generate the appropriate level of NO.

The flow meter 104 may be arranged upstream of the NO generator 102 and may be configured to measure a flow rate of gas in the breathing tube 400. The flow meter 104 may be in communication with the controller 108. In operation, the controller 108 may be configured to alter the electrical signal output to the power supply 106, and thereby the electric discharge characteristics of the electrodes 202 (i.e., the NO gas concentration produced), in response to the measurements of the flow meter 104 and the gas and pressure sensors 406. Additionally, the controller 108 may be configured to detect inspiration and expiration of the patient based on the measurements of the flow meter 104 and/or the gas sensors 406. The detection of inspiration and/or expiration may be used to trigger the NO generator 102 to generate NO gas upon inspiration and avoid generating NO during exhalation saving energy, as will be described in detail below.

The controller 108 can include a transceiver 408 and a communication port. The controller 108 can be configured to communicate wirelessly, via the transceiver 408, with an external processor (not shown) and/or a display (not shown) using Bluetooth®, WiFi, or any wireless communication protocol known in the art or developed in the future. Alternatively or additionally, the controller 108 can be configured to communicate, via the communication port, with the external processor (not shown) and/or the display (not shown) using a universal serial bus (USB) connection, an Ethernet connection, or any wired communication protocol known in the art or developed in the future.

Figure 6:
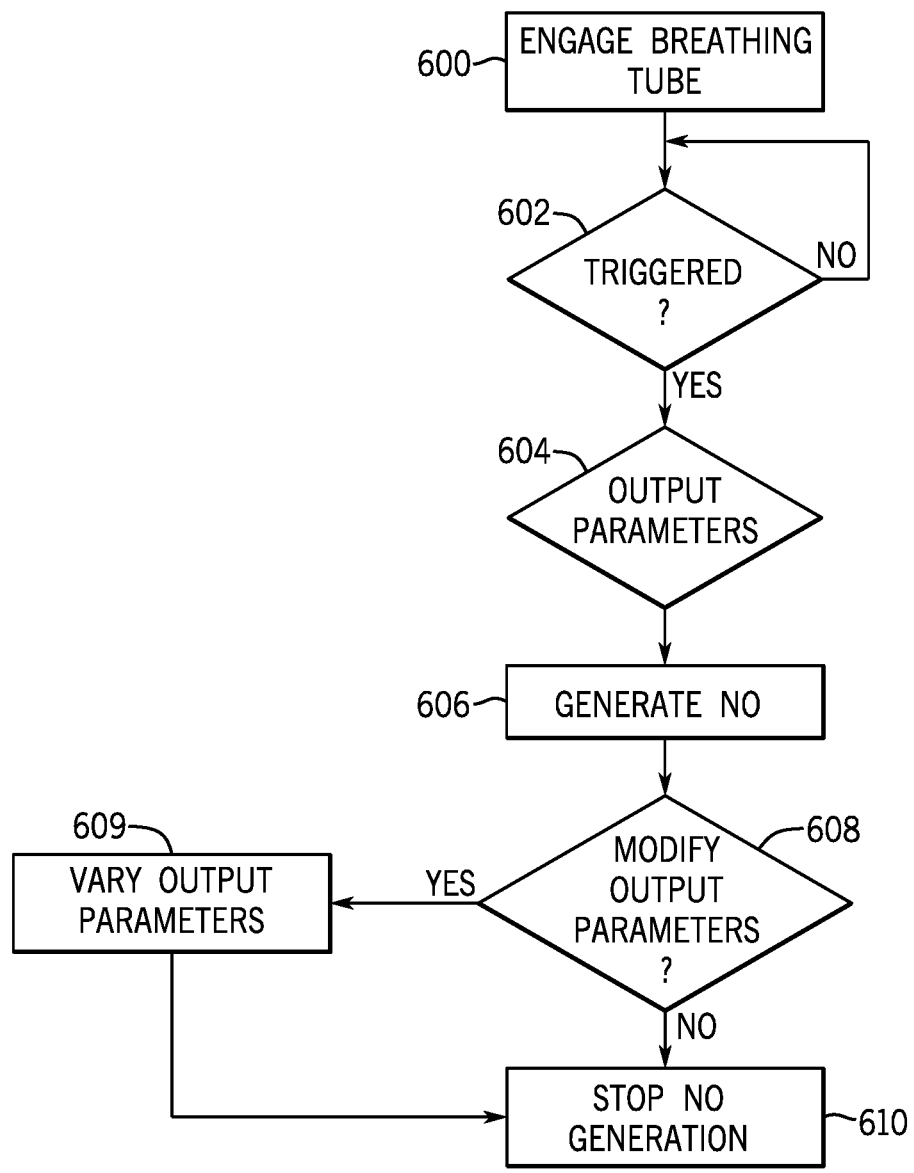
FIG. 6 shows a flow chart illustrating some examples of steps for operating the nitric oxide generation system of FIG. 4 according to one aspect of the present disclosure.

As described above, the NO generation system 100 may be configured to generate NO gas at the point of care (i.e., at, or in, the breathing tube 402) while simultaneously providing a chemically and thermally safe output flow to the patient. One great advantage of synthesizing NO at the breathing tube is to avoid wasting NO by generating NO for the large bias flow of a ventilator. Thus all the NO produced can directly enter the inspired gas stream. That is, the output flow from the NO generator 102 can include safe concentrations of $NO_2$ and $O_3$, and be filtered of potentially harmful particles. The operation of the NO generation system 100 will be described below by way of one or more non-limiting examples and with reference to FIGS. 1-6. As shown in FIG. 6, the NO generator 102 is engaged with the breathing tube 402 at step 600. Preferably, the second wall 208 of the NO generator 102 is placed in fluid communication with the breathing tube 402 at or near the distal end 400. With the NO generator 102 engaged with the breathing tube 402, the controller 108 may be configured to monitor the flow meter 104 and the gas sensors 406 to detect a triggering event at step 602. In an exemplary non-limiting example, the controller 108 may be configured to detect inspiration of a patient, for example via the flow meter 104 and/or a pressure or temperature upstream of the NO generator 102, and then trigger the power supply 106 to supply the discharge voltage to the electrodes 202 after the onset of inspiration. Triggering the NO generator 102 after the onset of inspiration ensures that the scavenger 222, which is in fluid communication with the breathing tube 402, is not exposed to high concentrations of $CO_2$ (e.g., up to 50,000 ppm or more) present during exhalation that could potentially consume the scavenger 222.

Once triggered at step 602, the controller 108 may be configured to determine desired output parameters based on a desired output concentration of NO to be supplied to the patient. The output parameters, provided by an electrical signal via the power supply 106, can be sent to the electrodes 202 at step 604 to energize the electrodes 202. In one non-limiting example, the controller 108 can determine the parameters of the electrical signal based on at least one or more of atmospheric pressure, temperature, humidity, and oxygen concentration. Additionally or alternatively, the electrical signal can be determined using the B, N, P, and H characteristics, described above. Further, the concentration of NO to be supplied to a patient may be determined based on at least one of a body mass index (BMI), weight, respiratory tidal volume or minute ventilation rate or another physical characteristic of the patient. Once determined, the level of NO delivered to the patient may be provided in micromoles per breath, or micromoles per minute, for example. Further still, the concentration of NO to be supplied to the patient may be manually input to the controller 108.

With the desired output parameters for a given concentration or dose of NO determined at step 604, the controller 108 then sends the corresponding electrical signal via the power supply 106 to the electrodes 202 to initiate a series of electric plasma discharges. The series of electric plasma discharges induce a chemical reaction between the electrodes 202 that generates a desired concentration of NO gas at step 606. The series of electric plasma discharges initiated between the electrodes 202 at step 606 instantaneously release electrical energy into the gas to produce a plasma within the housing 204 and induces pressure imbalances as the temperature in the plasma rises to approximately 1000-2000 degrees Kelvin. These pressure imbalances induced by the electric plasma discharge between the electrodes 202 drive thermal expansion and convective transport of the generated NO gas into the breathing tube 402. That is, the design of the NO generator 102 non-mechanically directs the generated NO gas along the flow path through the second wall 208 and then to the airway of the patient. The concept of non-mechanically directing the generated NO is one that does not require the use of an additional device (e.g., a pump, a fan, etc.) to drive the flow of the NO laden gas to a patient. Instead, the NO generator 102 leverages transport phenomena occurring during the electric plasma discharge between the electrodes 202 to direct the generated NO laden gas within the housing 204 along the flow path and then to the breathing tube 402. Further, the geometric design of the NO generator 102 can assist in the convective transport of the generated NO laden gas by defining a volume between the housing 204 and the insulator 212 (i.e., the reaction chamber 213) that is sufficiently small to ensure substantially instantaneous delivery of the generated NO laden gas to a patient (i.e., the generated NO laden gas is delivered to the airway of a patient within early inspiration). In this way, the NO generator 102 provides supplemental flow laden with the generated NO gas to the patient and is not required to provide a bias flow and/or generate additional NO gas to supplement the bias flow requirement.

While the desired concentration of NO gas is being delivered to the patient at step 606, the controller 108 may be configured to monitor the feedback it receives from the gas sensors 406 and or the flow meter 104. Based on the feedback, the controller 108 may be configured to determine if the electric output parameters need to be modified at step 608. For example, the controller 108 can detect, via the gas sensors 406, that the generated NO concentration or dose is deviating from a desired NO concentration or dose and adjust the output parameters sent to the electrodes 202 accordingly. Alternatively or additionally, the controller 108 may be configured to monitor electric discharge current from the electrodes 202 in order to verify that NO generation is occurring. If the controller 108 determines that the NO concentration generated by the NO generator 102 needs adjusting, the controller 108 can modify the output parameters applied to the power supply 106 accordingly at step 609.

The controller 108 may be configured to stop the generation of NO gas after a pre-determined amount of time at step 610. In one exemplary non-limiting example, the controller 108 may be configured to stop the generation of NO gas during inspiration to allow immediate cooling and aspiration of fresh, $CO_2$ free, gas into the NO generator 102. This can cool the gas within the housing 204 and prevent $NO_2$ from forming in the stagnant gas in the reaction chamber 213.

The above-described steps 602-610 can be repeated for each triggering event to continually supply pure and safe NO laden gas to a patient. That is, in one non-limiting example, the NO generator 102 can be triggered during the onset of inspiration and generate a desired concentration or dose of NO laden gas which is convectively transported to the patient for a pre-determined amount of time until the NO generator is stopped before the end of inspiration.

The above-described techniques and properties of the NO generation system 100 enable the generation of pure and safe NO laden gas to be supplied to a patient at or in a breathing tube (i.e., at a point of care). Placing the NO generator 102 at, or in, a breathing tube eliminates the requirement of the NO generation system 100 to supply a large bias gas flow thereby substantially reducing the power requirement, thermal energy generation, and NO generation requirement. Additionally, the placement of the NO generator 102 at, or in, a breathing tube reduces the transport time for the NO laden gas to travel from the NO generator 102 to the airway of the patient. Reducing the transport time reduces a probability of NO oxidizing to $NO_2$ in the oxygen rich environment. Thus, the placement of the NO generator 102 at, or in, a breathing tube further enables the NO generation system 100 to provide accurate concentrations of NO to a patient such that the NO concentration delivered to the patient is predictable.

In another non-limiting configuration, the NO generation system 100 can be integrated into a portable system, similar to a diabetic pump, that can be worn by a patient to supply therapeutic concentrations of pure NO gas to the patient. In this non-limiting configuration, the NO generator 102 can be coupled, for example, to a nasal breathing tube worn by the patient. The controller 108 can be configured to supply the therapeutic concentrations of NO gas to the patient at pre-determined periods of time or when triggered, for example, by the patients blood oxygen concentration.

EXAMPLES

The following examples set forth, in detail, ways in which the NO generation system 100 and/or the NO generator 102 may be used or implemented, and will enable one of skill in the art to more readily understand the principle thereof. The following examples are presented by way of illustration and are not meant to be limiting in any way.

Example 1: Measuring NO Generation as a Function of Power Input

Figure 7:
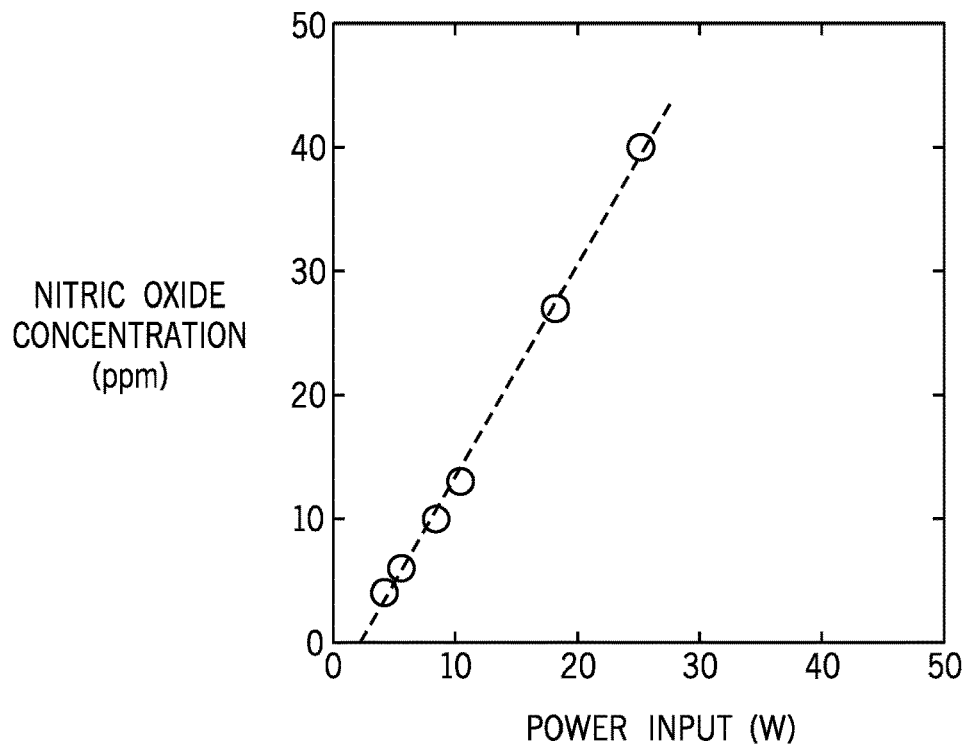
FIG. 7 shows a graph illustrating nitric oxide concentration generated by the nitric oxide generation system of FIG. 4 as a function of power input.

The NO generator 102 was tested at varying levels of power input to the electrodes 202 by the power supply 106 and the resulting output concentration of NO was measured. The NO concentrations generated by the NO generator 102 were measured at a constant gas flow of 5 L/min. FIG. 7 shows the NO concentrations generated during the test. As shown in FIG. 7, the NO concentration generated by the NO generator 102 increased substantially linearly with increased power input. The NO concentration generated varied from approximately 5 ppm to approximately 40 ppm over an input power range of approximately 3 watts (W) to 30 W, respectively. The data in FIG. 7 was generated using a flyback power supply. As described above, in some non-limiting examples, the power supply 106 may be a resonant power supply which are inherently more efficient than flyback power supplies. With the use of a resonant power supply, the energy consumption for the NO generator 102 drops to between approximately 2 W and 3 W for generating 40 ppm of NO.

Example 2: Measuring NO and $NO_2$ Concentrations as a Function of Time

Figure 8:
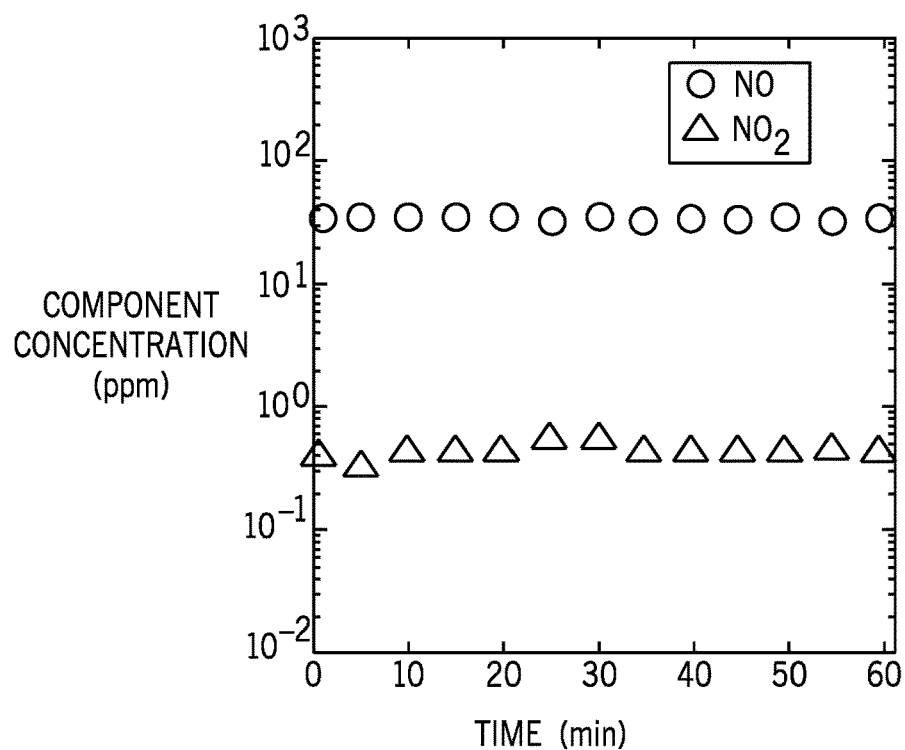
FIG. 8 shows a graph illustrating nitric oxide and nitrogen dioxide concentrations generated by the nitric oxide generation system of FIG. 4 as a function of time.

The NO generator 102 was tested when the controller 108 supplied a constant electrical signal to the power supply 106 at a constant gas flow rate of 5 L/min. As shown in FIG. 8, the NO generator 102 generated a substantially constant NO concentration of approximately 30 ppm over the 60 minute duration of the test. The $NO_2$ concentrations were between approximately 0.3 ppm and approximately 0.5 ppm over the duration of the test. Thus, the NO generator 102 produces safe (i.e., below the Environmental Protection Agency (EPA) limit) levels of $NO_2$ while maintaining a substantially constant output of NO gas.

Example 3: Demonstration Using the NO Generation System 200 on an Awake Sheep Animal studies were approved by the Institutional Animal Care and Use Committee of Massachusetts General Hospital (Boston, Mass.). The NO generator 102 of the NO generation system 100 was coupled to a tracheostomy tube in a spontaneously breathing awake 35 kg sheep.

To induce pulmonary hypertension, a potent pulmonary vasoconstrictor U46619 (Cayman Chemical, Ann Arbor, Mich.), the analog of the endoperoxide prostaglandin $H_2$, was infused intravenously to increase pulmonary arterial pressure (PAP) to 30 mmHg. The pulmonary arterial pressure and PAP was continuously monitored using a Gould 6600 amplifier system (Gould Electronics, Inc., Eastlake, Ohio).

Figure 9:
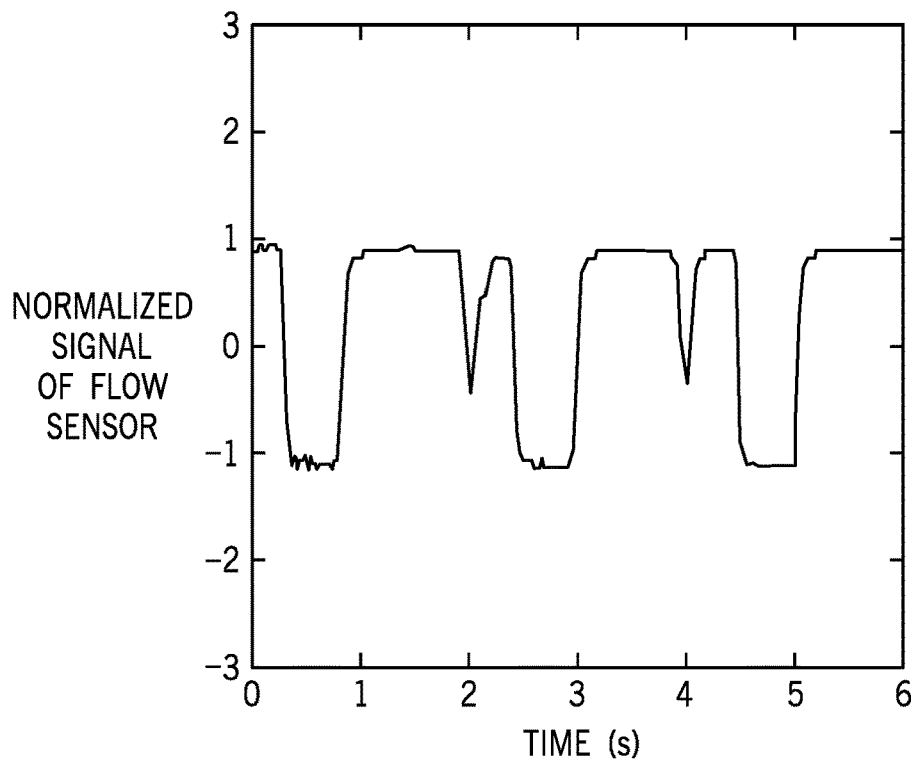
FIG. 9 shows a graph illustrating a normalized flow sensor signal as a function of time during testing of the nitric oxide generation system of FIG. 4 on an awake sheep with a tracheostomy.
Figure 10:
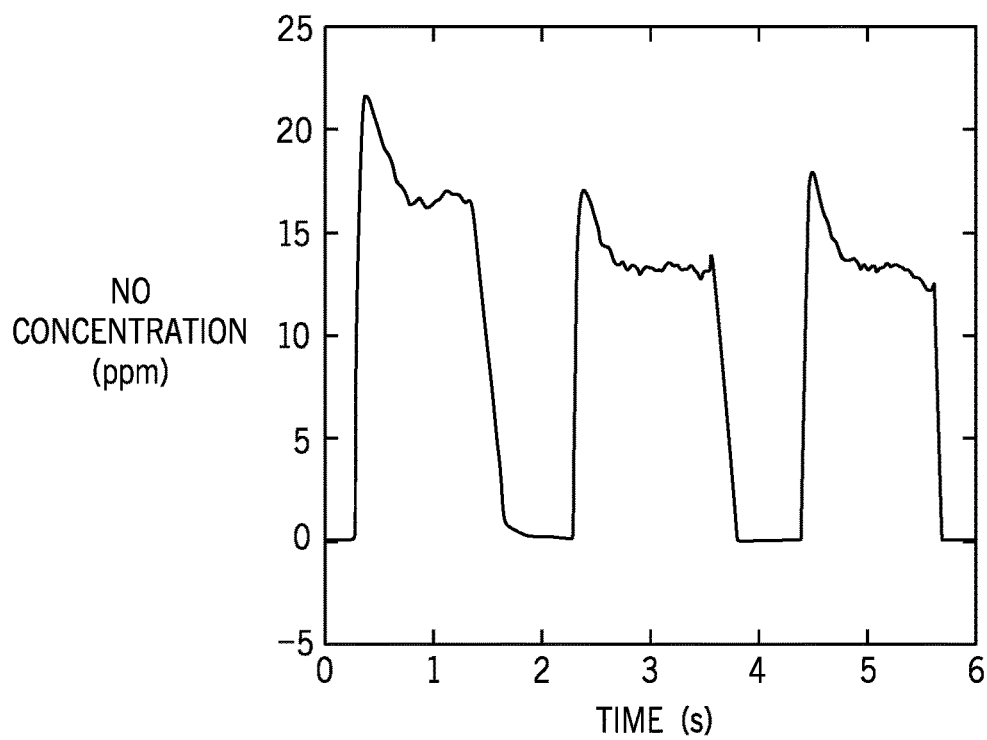
FIG. 10 shows a graph illustrating nitric oxide concentration generated by the nitric oxide generation system of FIG. 4 on an awake sheep as a function of time.

As shown in FIGS. 9 and 10, the controller 108 was configured to trigger the power supply 106 to supply the discharge voltage to the electrodes 202 for approximately 0.8 seconds during inspiration. That is, when the normalized flow signal, as shown in FIG. 9, step changes to a negative value, the controller 108 instructed the power supply 106 to supply the discharge voltage to the electrodes for approximately 0.8 seconds thereafter. In turn, the electric plasma discharge of the electrodes supplied NO gas to the spontaneously breathing awake sheep during those 0.8 seconds.

Figure 11:
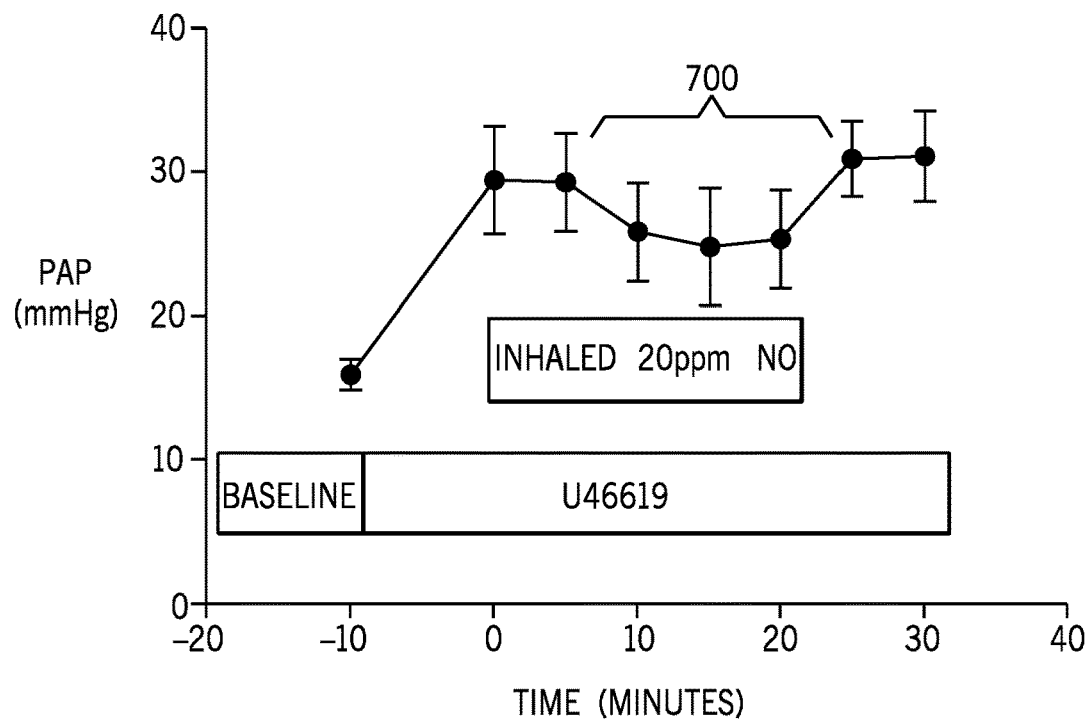
FIG. 11 shows a graph illustrating the pulmonary artery pressure (PAP) as a function of time in an awake sheep with acute pulmonary hypertension, due to U46619 infusion, inhaling 20 parts per million (ppm) of nitric oxide gas generated by the nitric oxide generation system of FIG. 4.
Figure 12:
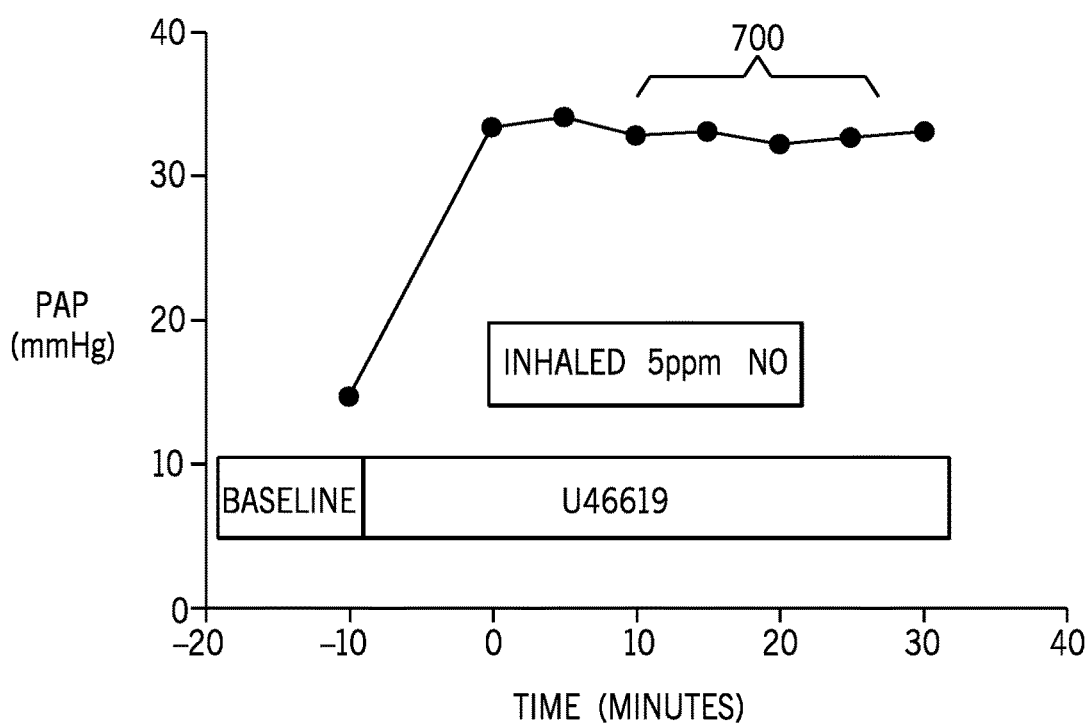
FIG. 12 shows a graph illustrating the pulmonary artery pressure (PAP) as a function of time in an awake sheep with acute pulmonary hypertension, due to U46619 infusion, inhaling 5 parts per million (ppm) of nitric oxide gas generated by the nitric oxide generation system of FIG. 4.

Turning to FIGS. 11 and 12, the above-described operation of the NO system 200 (i.e., triggering the NO generator 102 for approximately 0.8 second during early inspiration, for example, 20 milliseconds after commencement of inspiration) was implemented during a NO exposure time 700. Prior to and following the NO exposure time 700, a baseline was generated. The NO generator 102 was configured to output approximately 20 ppm of NO for three different runs (FIG. 11) and was configured to output 5 ppm of NO for another run (FIG. 12). As shown in FIG. 11, for each run where the NO generator output 20 ppm over the NO exposure time 700, the pulmonary artery pressure (PAP) of the anesthetized sheep reduced by approximately 4 to 6 millimeters of mercury (mmHg) during the NO exposure time 700. As shown in FIG. 12, the PAP of the anesthetized sheep does not show a measurable effect during the NO exposure time 700 at 5 ppm of NO.

Figure 13:
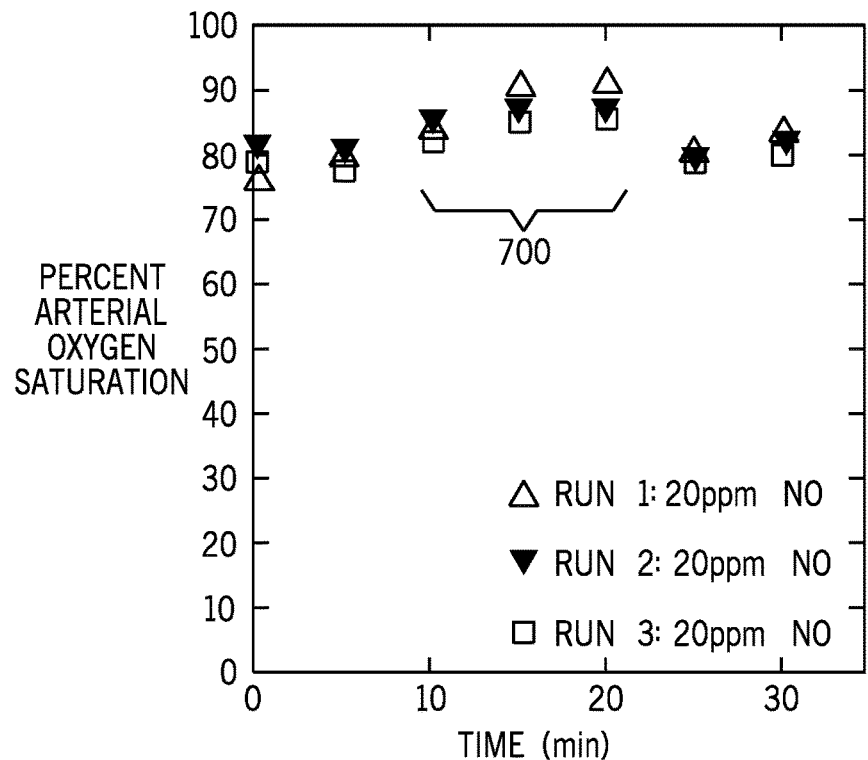
FIG. 13 shows a graph illustrating the arterial oxygen saturation (SaO2) as a function of time in an awake sheep with acute pulmonary hypertension, due to U46619 infusion, inhaling 20 parts per million (ppm) of nitric oxide gas generated by the nitric oxide generation system of FIG. 4.
Figure 14:
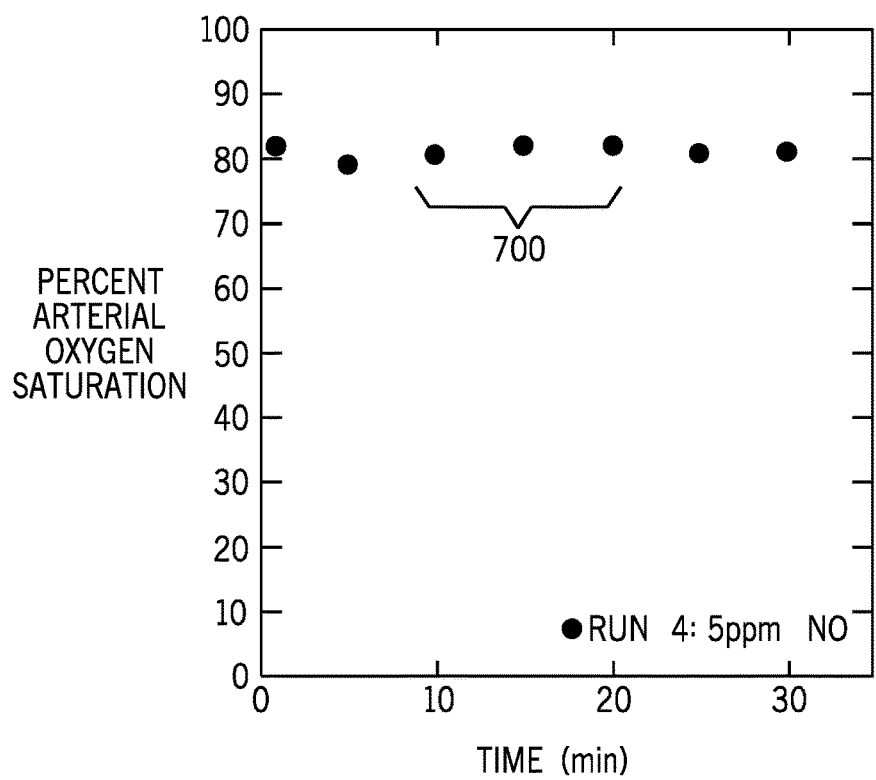
FIG. 14 shows a graph illustrating the arterial oxygen saturation (SaO2) as a function of time in an awake sheep with acute pulmonary hypertension, due to U46619 infusion, inhaling 5 parts per million (ppm) of nitric oxide gas generated by the nitric oxide generation system of FIG. 4.
Figure 15:
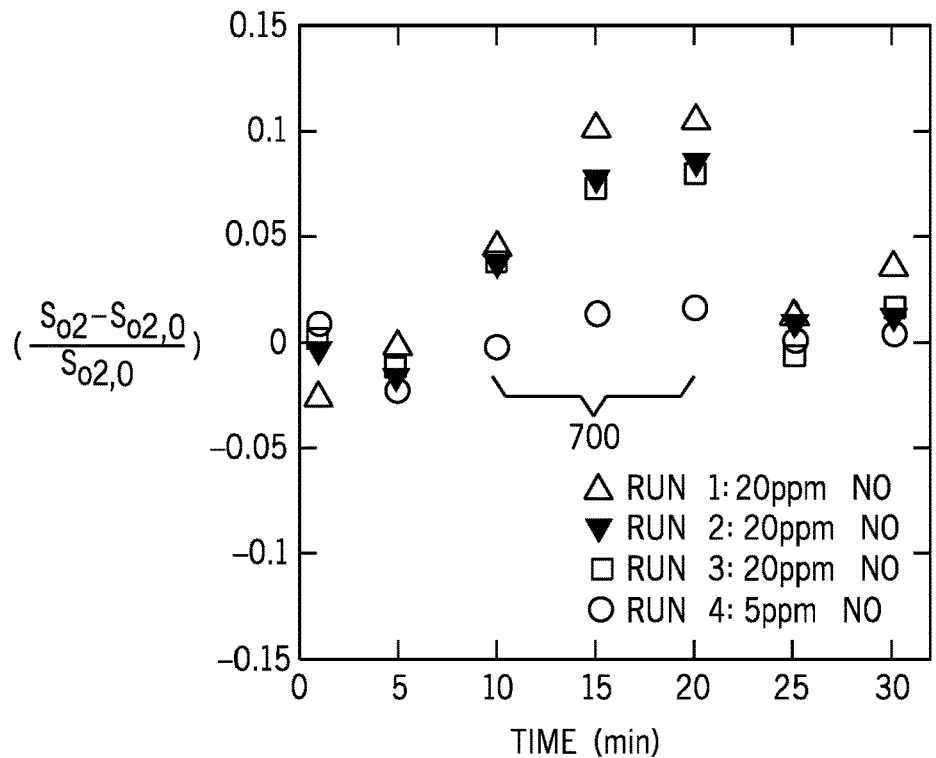
FIG. 15 shows a graph illustrating the relative arterial oxygen saturation as a function of time in an awake sheep with acute pulmonary hypertension, due to U46619 infusion, inhaling various concentrations of nitric oxide gas generated by the nitric oxide generation system of FIG. 4.

In addition to PAP, the arterial oxygen saturation was also measured as a function of time in the awake sheep. As shown in FIG. 13, the arterial oxygen saturation increases for delivery of 20 ppm NO during the window of time 700. However, as shown in FIG. 14, the arterial oxygen saturation, is generally constant during delivery of 5 ppm NO over the NO exposure time 700. Lastly, the relative arterial oxygen saturation was calculated as a function of time for all four periods of NO inhalation. As shown in FIG. 15, the relative arterial oxygen saturation improves by approximately 10% during the NO exposure time 700 for the three trials at 20 ppm.

Figure 16:
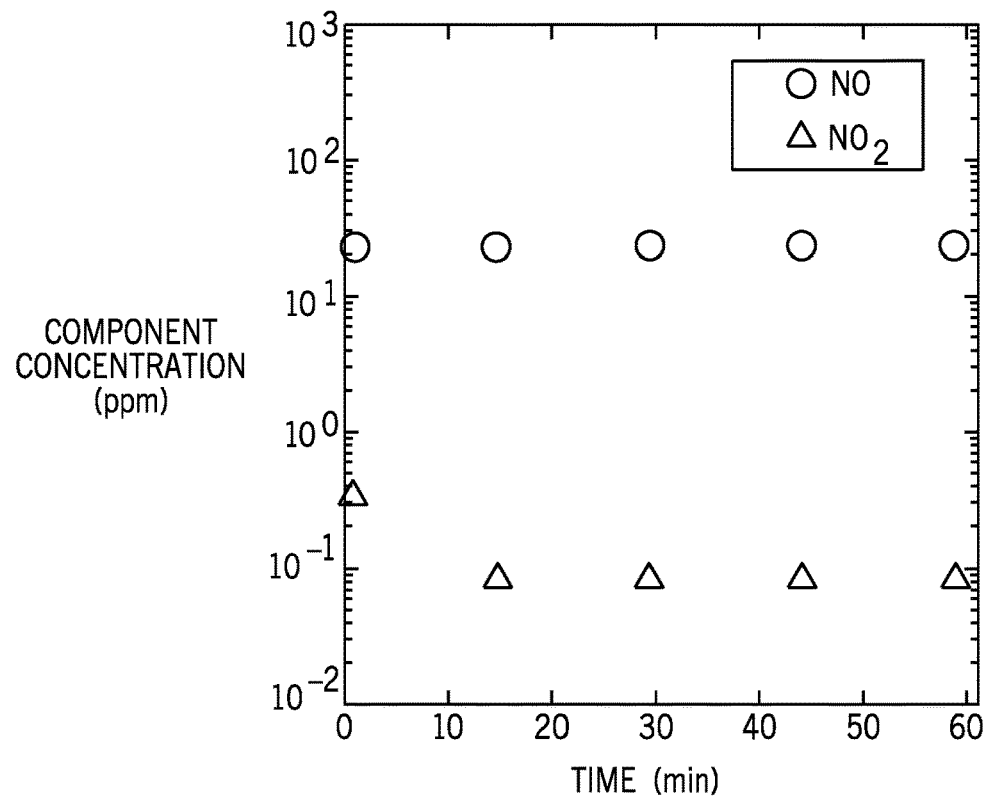
FIG. 16 shows a graph illustrating nitric oxide and nitrogen dioxide concentrations generated by the nitric oxide generation system of FIG. 4 after testing performed on an awake sheep as a function of time.

Example 4: Measuring NO and $NO_2$ Concentrations as a Function of Time after Sheep Studies The NO generator 102 was tested when the controller 108 supplied a constant electrical signal to the power supply 106 at a constant gas flow rate of 5 L/min. The settings of the controller 108 were similar to the test performed in Example 2 to determine if the sheep testing affected the performance of the NO generation system 100. As shown in FIG. 16, the NO generator 102 generated a substantially constant NO concentration of approximately 30 ppm over the 60 minute duration of the test, similar to the results shown in FIG. 8. The $NO_2$ concentrations were reduced from approximately 0.4 ppm to approximately 0-0.1 ppm. Thus, the performance of the NO generator 102 was not affected by exposure of the NO generation system 100 during all the sheep studies.

Figure 17:
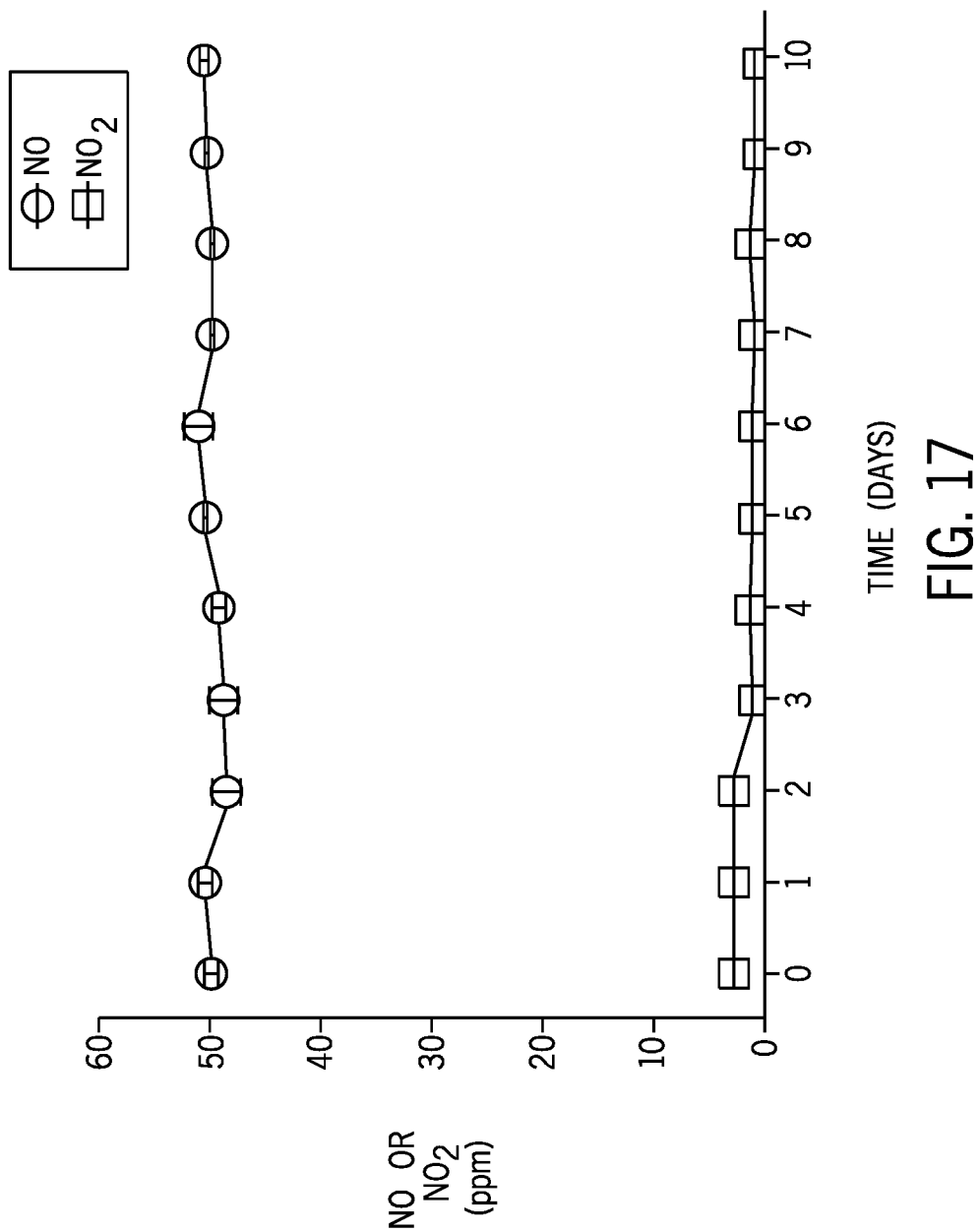
FIG. 17 shows a graph illustrating nitric oxide and nitrogen dioxide concentrations generated by the nitric oxide generation system of FIG. 4 over a ten day test on the lab bench.

Example 5: Measuring NO and $NO_2$ Concentrations During Continuous Lab Bench Operation for 10 Days The NO generator 102 was tested at a constant operation condition where the controller 108 instructed the power supply 106 to discharge the electrodes 202 and produce approximately 50 ppm of NO. The electrodes 202 were fabricated from iridium-platinum. The controller 108 was configured to spark the electrodes 202 using the following settings to produce approximately 50 ppm of NO: B=20, N=20, P=240 µs; and H=70 µs. FIG. 17 shows the NO and $NO_2$ concentrations generated by the NO generator over the 10 day test. As shown in FIG. 17, the NO and $NO_2$ concentrations remained substantially constant over the 10 days.

Figure 18:
FIG. 18 shows air breathing chambers that were fed either 50 ppm of nitric oxide gas in air or air alone that was used to test on mice (C57BL6 male WT).

Example 6: Comparison of Mice Breathing Air and Electrically Generated 50 ppm NO in Air for 28 Days FIG. 18 shows a breathing chamber test setup used for the mice studies. As shown in FIG. 18, a first chamber 800 was supplied with air and a plurality of mice (C57BL6 male WT) breathed the supplied air for 28 days. A second chamber 802 was supplied with 50 ppm of NO gas in air, generated by a spark plug generator using platinum-iridium electrodes and subsequently scavenged using 75 g Ca(OH). A plurality of mice (C57BL6 male WT) breathed the NO laden air for the same 28 day period. During the 28 day test, humidity, $CO_2$, $O_2$, NO, and $NO_2$ were monitored intermittently.

Figure 19:
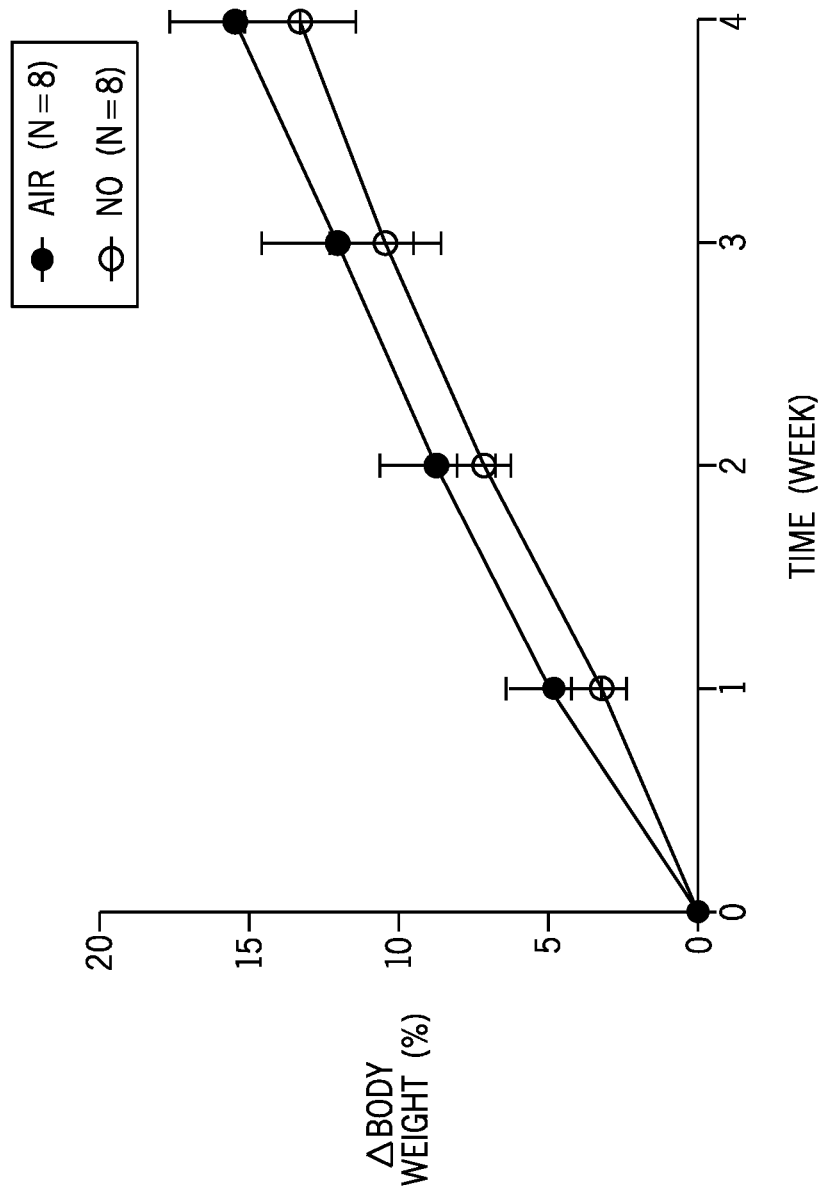
FIG. 19 shows a graph illustrating an average change in body weight of the mice breathing air alone or air with 50 ppm of NO in the chambers of FIG. 18 over a twenty eight day test.

Throughout the 28 day test, the mice were weighed in weekly intervals to track a change in the body weight of the mice throughout the 28 day test. As shown in FIG. 19, the body weight gain of the mice did not differ in mice either breathing air or 50 ppm of electrically generated NO in air over the 28 day test. Once the 28 day test was complete, lung specimens from the mice were analyzed using a high resolution magnetic sector field inductively coupled mass spectrometer (Thermo Fisher, Bremen, Germany). Specifically, the mice lung specimens were analyzed for iridium and platinum to determine if the mice breathing electrically generated NO in air showed any signs of inhaling evaporated or eroded fragments from the electrodes. As shown in the table of FIG. 20, no detectable difference was measured between the lung specimens of the control mice (i.e., the mice that breathed air for 28 days) and the lung specimens of the mice that breathed 50 ppm of electrically generated NO in air for 28 days. Lung histology (H&E staining of the larynx, trachea, main bronchus, and lung tissues) showed no evidence of lung inflammation or pathology (i.e., no microphages or neutrophils, no epithelial cells stripping, no thickening wall, etc.) in the mice that breathed 50 ppm of electrically generated NO in air for 28 days.

Figure 21:
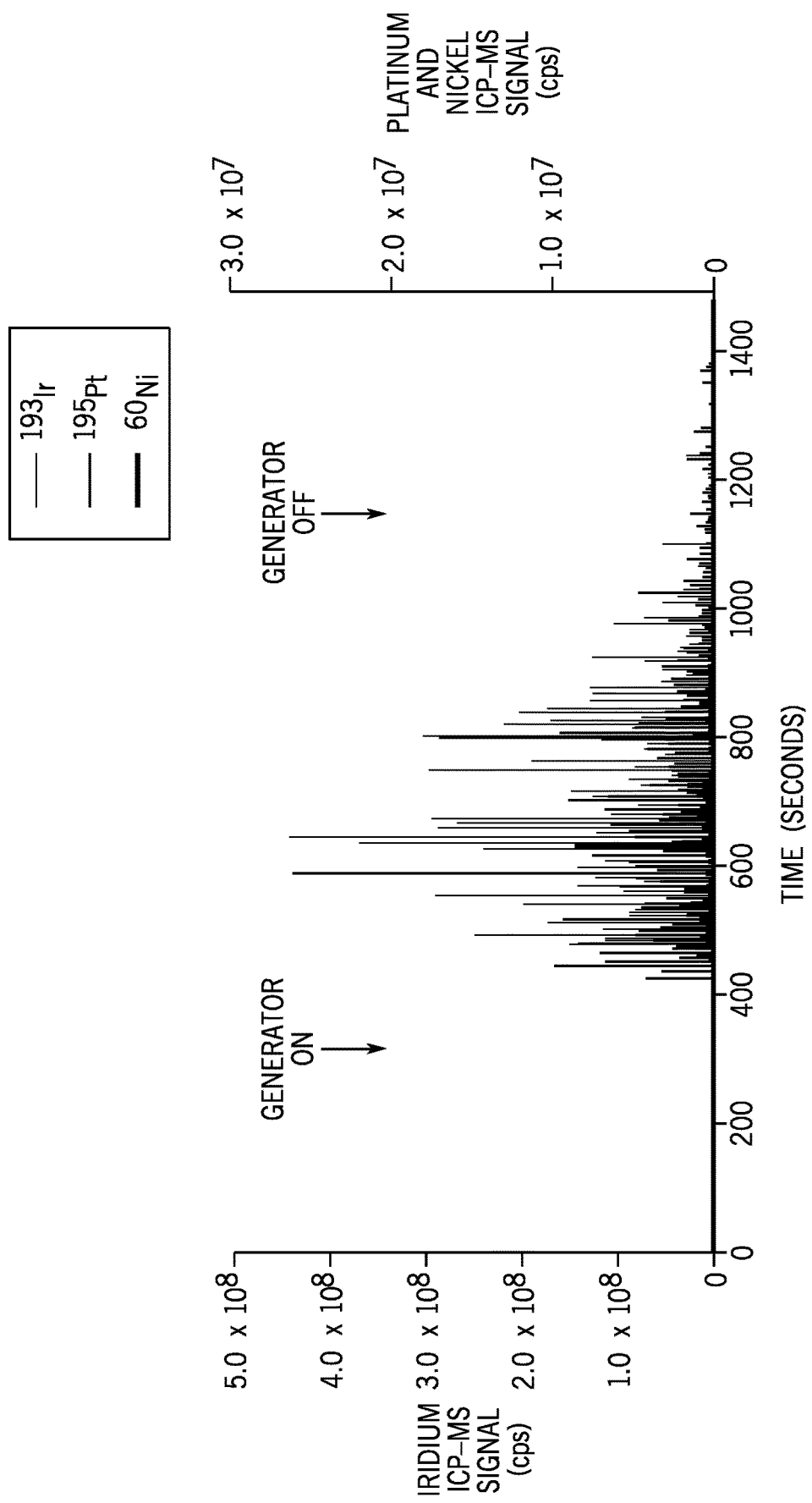
FIG. 21 shows a graph illustrating iridium, platinum, and nickel with high resolution inductive coupled plasma mass spectrometer results output from a spark plug generator in the absence of both a 0.22 micron HEPA filter and a scavenger.
Figure 22:
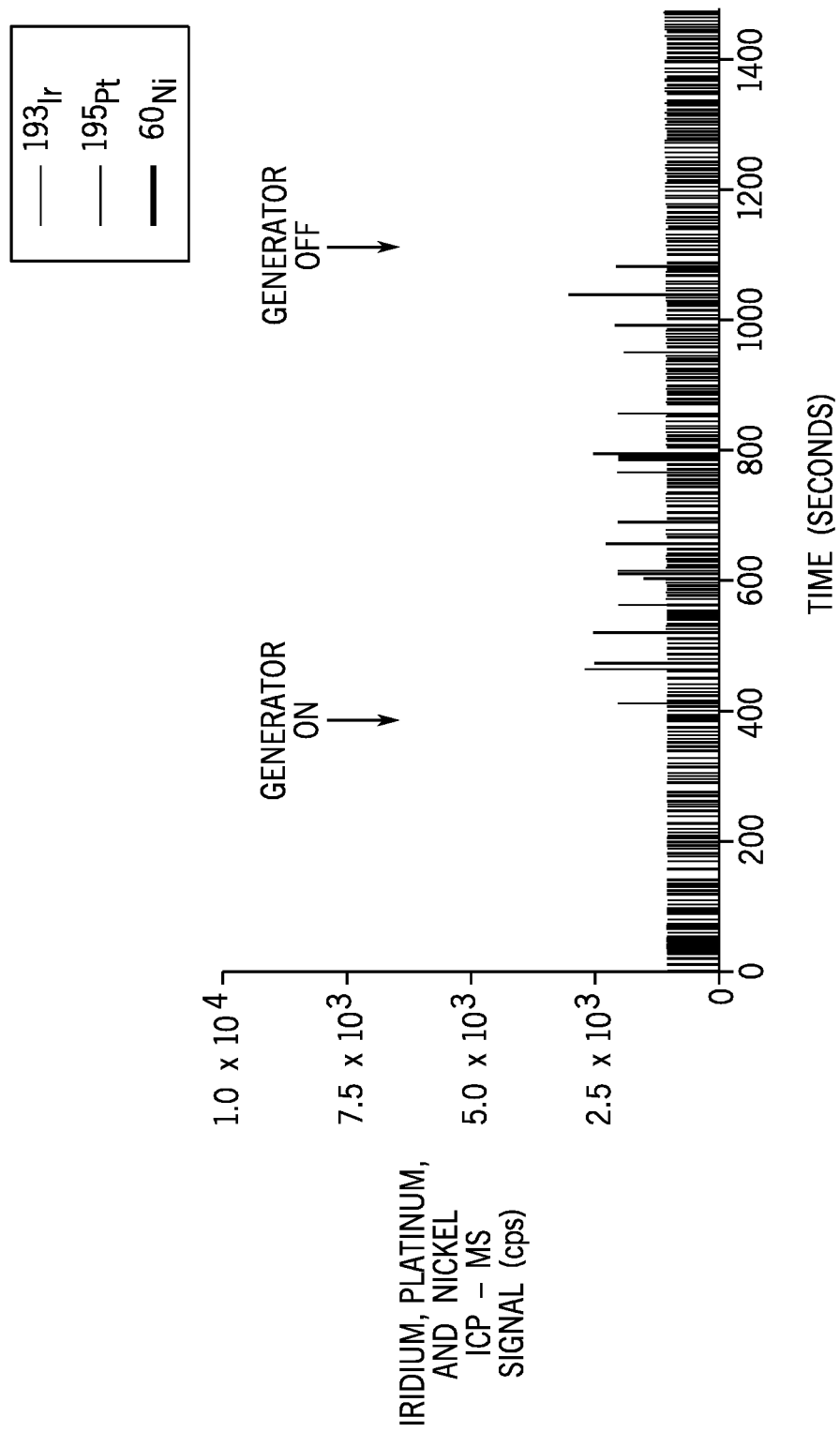
FIG. 22 shows a graph illustrating iridium, platinum, and nickel with high resolution inductive coupled plasma mass spectrometer results output from a spark plug generator followed by only a 12 g Ca(OH)$_2$ scavenger.
Figure 23:
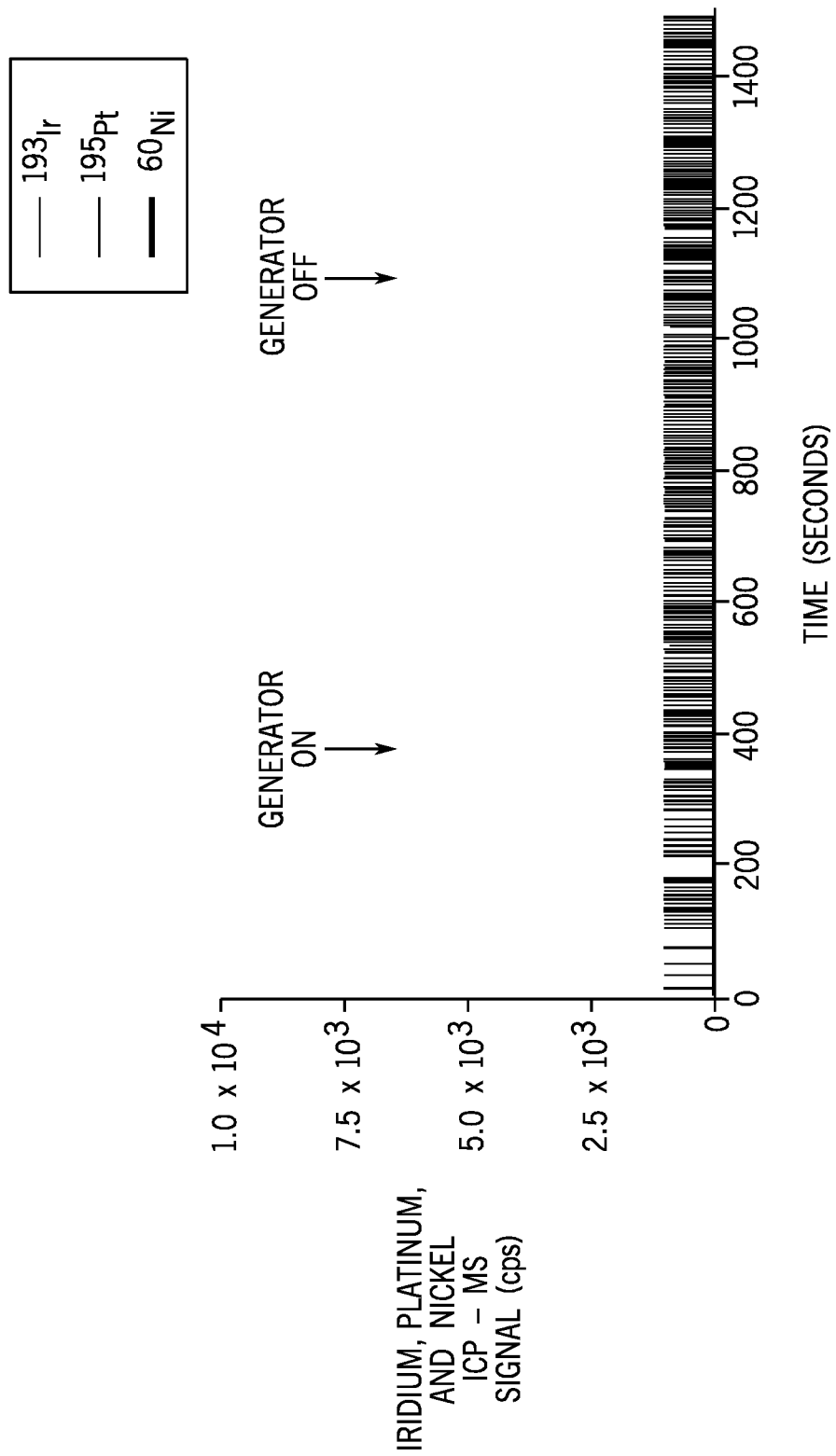
FIG. 23 shows a graph illustrating iridium, platinum, and nickel with high resolution inductive coupled plasma mass spectrometer results output from a spark plug generator followed with both a 0.22 micron HEPA filter and a 12 g $Ca(OH)_2$ scavenger.

Example 7: Mass Spectrometer Analysis of the Output Flow from a Spark Plug Generator Using Iridium-Platinum Electrodes The spark plug generator was tested at a flow rate of 50 milliliters per minute using platinum-iridium electrodes and the output flow was coupled to a high resolution magnetic sector field inductively coupled mass spectrometer (Thermo Fisher, Bremen, Germany). The output flow was sampled by the mass spectrometer without a scavenger, and without a 0.22 um HEPA filter, similar to the particle filter 224 (FIG. 21). Additionally, the output flow was sampled by the mass spectrometer with only a 12 g Ca(OH)$_2$ scavenger (FIG. 22), and with both the 12 g Ca(OH)$_2$ scavenger and the 0.22 um HEPA filter (FIG. 23).

For each of the tests, the spark plug generator was instructed to generate NO gas for a period of time, then the spark plug generator was turned off and the mass spectrometer measured the chemical composition of the output flow. As shown in FIG. 21, the mass spectrometer detected platinum, iridium, and nickel in the resulting output flow (without any filtration or scavenging). As shown in FIG. 22, with only the 12 g Ca(OH)$_2$ scavenger added between the mass spectrometer and the spark plug generator, only minimal amounts of iridium, platinum, and nickel metal particles were detected by the mass spectrometer. As shown in FIG. 23, with the 0.22 um HEPA filter and the 12 g Ca(OH)$_2$ scavenger added between the mass spectrometer and the spark plug generator no iridium, platinum, or nickel particles were detected by the mass spectrometer. Thus, an 0.22 um HEPA filter is sufficient to block all metal particles from the electrodes during operation of the spark plug generator.

Whilst the invention has been described above, it extends to any inventive combination of features set out above or in the following description. Although illustrative embodiments of the invention are described in detail herein with reference to the accompanying drawings, it is to be understood that the invention is not limited to these precise embodiments. Furthermore, it is contemplated that a particular feature described either individually or as part of an embodiment can be combined with other individually described features, or parts of other embodiments, even if the other features and embodiments make no mention of the particular feature. Thus, the invention extends to such specific combinations not already described.

While the invention has been described above in connection with particular embodiments and examples, the invention is not necessarily so limited, and that numerous other embodiments, examples, uses, modifications and departures from the embodiments, examples and uses are intended to be encompassed by the claims attached hereto. The entire disclosure of each patent and publication cited herein is incorporated by reference, as if each such patent or publication were individually incorporated by reference herein.

We claim:

1. An apparatus for generating nitric oxide comprising:
a housing including a first wall having an aperture formed therein to provide access to a recess and a second wall permitting gas flow therethrough;
an insulator arranged in the recess, wherein the insulator defines a cavity;
two or more electrodes arranged within the insulator so that each of the two or more electrodes abuts a surface of the insulator that defines the cavity, and wherein the surfaces of the insulator that the two or more electrodes abut are spaced to define a spark gap between the two or more electrodes;
a power supply connected to the two or more electrodes to energize the two or more electrodes to induce a chemical reaction within the recess that generates nitric oxide;
a particle filter arranged to filter particulates from passing through the second wall;
a scavenger arranged proximate to the particle filter to control an amount of undesired byproducts from the chemical reaction induced by operation of the two or more electrodes;
a controller in communication with the power supply and configured to selectively energize the two or more electrodes to achieve one or more electric discharges between the two or more electrodes to generate the nitric oxide within the housing; and
a flow path configured to direct the nitric oxide toward the second wall of the housing and into an airway, wherein the nitric oxide is non-mechanically directed along the flow path;
wherein the housing includes a plurality of layers,
wherein the plurality of layers include a first layer, a second layer, and a third layer, wherein the second layer is arranged between the first layer and the third layer, and
wherein the first layer and the third layer are fabricated from an electrical insulating material with a lower thermal conductivity than the second layer.

2. The apparatus of claim 1, wherein the flow path leverages transport phenomena occurring during the one or more electric discharges between the two or more electrodes to non-mechanically direct the nitric oxide through the second wall of the housing and into the airway.

3. The apparatus of claim 2, wherein the transport phenomena comprise convective transport.

4. The apparatus of claim 1, wherein a volume between the housing and the insulator defines a reaction chamber that is sufficiently small to ensure substantially instantaneous delivery of the nitric oxide along the flow path to the airway.

5. The apparatus of claim 1, wherein the two or more electrodes comprise at least one of tungsten carbide, carbon, nickel, iridium, titanium, rhenium, and platinum.

6. The apparatus of claim 1, wherein the two or more electrodes comprise iridium.

7. The apparatus of claim 1, wherein the power supply comprises a resonant high-voltage power supply or a synchronous power supply.

8. The apparatus of claim 1, wherein the particle filter is configured to filter particles with a diameter greater than approximately 0.22 micrometers.

9. The apparatus of claim 1, wherein the particle filter comprises a HEPA filter.

10. The apparatus of claim 1, wherein the second layer is connected to a heat sink.

11. The apparatus of claim 1, wherein the controller is configured to detect an onset of inspiration and selectively energize the two or more electrodes to achieve the one or more electric discharges after the onset of inspiration is detected.

12. An apparatus for generating nitric oxide comprising:
a housing including a first wall having an aperture formed therein to provide access to a recess and a second wall permitting gas flow therethrough;
an insulator arranged in the recess, wherein the insulator defines a cavity;
a reaction chamber defined by a volume between the housing and the insulator;

two or more electrodes arranged within the insulator so that each of the two or more electrodes abuts a surface of the insulator that defines the cavity, and wherein the surfaces of the insulator that the two or more electrodes abut are spaced to define a spark gap between the two or more electrodes;
a power supply connected to the two or more electrodes to energize the two or more electrodes to induce a chemical reaction within the reaction chamber that generates nitric oxide;
a particle filter arranged to filter particulates from passing through the second wall;
a scavenger arranged proximate to the particle filter to control an amount of undesired byproducts from the chemical reaction induced by operation of the two or more electrodes; and
a controller in communication with the power supply and configured to selectively energize the two or more electrodes to achieve one or more electric discharges between the two or more electrodes to generate the nitric oxide within the reaction chamber;
wherein the second wall is dimensioned to engage a breathing tube and the reaction chamber is configured to direct the nitric oxide toward the second wall and into the breathing tube,
wherein the housing includes a plurality of layers,
wherein the plurality of layers include a first layer, a second layer, and a third layer, wherein the second layer is arranged between the first layer and the third layer, and
wherein the first layer and the third layer are fabricated from an electrical insulating material with a lower thermal conductivity than the second layer.

13. The apparatus of claim 12, wherein the nitric oxide is nonmechanically directed through the second wall and into the breathing tube.

14. The apparatus of claim 12, wherein the reaction chamber leverages transport phenomena occurring during the one or more electric discharges between the two or more electrodes to direct the nitric oxide through the second wall and into the breathing tube.

15. The apparatus of claim 14, wherein the transport phenomena comprise convective transport.

16. The apparatus of claim 12, wherein the reaction chamber is sufficiently small to ensure substantially instantaneous delivery of the nitric oxide to the breathing tube.

17. The apparatus of claim 12, wherein the two or more electrodes comprise at least one of tungsten carbide, carbon, nickel, iridium, titanium, rhenium, and platinum.

18. The apparatus of claim 12, wherein the two or more electrodes comprise iridium.

19. The apparatus of claim 12, wherein the power supply comprises a resonant high-voltage power supply or a synchronous power supply.

20. The apparatus of claim 12, wherein the particle filter is configured to filter particles with a diameter greater than approximately 0.22 micrometers.

21. The apparatus of claim 12, wherein the particle filter comprises a HEPA filter.

22. The apparatus of claim 12, wherein the second layer is connected to a heat sink.

23. The apparatus of claim 12, wherein the controller is configured to detect an onset of inspiration and selectively energize the two or more electrodes to achieve the one or more electric discharges after the onset of inspiration is detected.

24. An apparatus for generating nitric oxide, the apparatus comprising:
a housing including a first wall having an aperture formed therein to provide access to a recess and a second wall permitting gas flow therethrough and in fluid communication with a breathing tube;
an insulator arranged in the recess, wherein the insulator defines a cavity;
two or more electrodes arranged within the insulator so that each of the two or more electrodes abuts a surface of the insulator that defines the cavity, and wherein the surfaces of the insulator that the two or more electrodes abut are spaced to define a spark gap between the two or more electrodes;
a power supply connected to the two or more electrodes to energize the two or more electrodes to induce a chemical reaction within the recess that generates nitric oxide;
a particle filter arranged to filter particulates from passing through the second wall;
a scavenger arranged proximate to the particle filter to control an amount of undesired byproducts from the chemical reaction induced by operation of the two or more electrodes;
one or more sensors arranged downstream of the two or more electrodes to measure at least one of a nitric oxide concentration, a nitrogen dioxide concentration, an oxygen concentration, a carbon dioxide concentration, and a pressure;
a flow meter configured to measure a flow rate within the breathing tube;
a controller in communication with the power supply, the one or more sensors, and the flow meter and configured to selectively energize the two or more electrodes to achieve one or more electric discharges between the two or more electrodes to generate nitric oxide within the housing; and
a flow path configured to direct the nitric oxide toward the second wall of the housing and into the breathing tube, wherein the nitric oxide is non-mechanically directed along the flow path,
wherein the housing includes a plurality of layers,
wherein the plurality of layers include a first layer, a second layer, and a third layer, wherein the second layer is arranged between the first layer and the third layer, and
wherein the first layer and the third layer are fabricated from an electrical insulating material with a lower thermal conductivity than the second layer.

25. The apparatus of claim 24, wherein the flow path leverages transport phenomena occurring during the one or more electric discharges between the two or more electrodes to non-mechanically direct the nitric oxide through the second wall of the housing and into the breathing tube.

26. The apparatus of claim 25, wherein the transport phenomena comprise convective transport.

27. The apparatus of claim 24, wherein a volume between the housing and the insulator defines a reaction chamber that is sufficiently small to ensure substantially instantaneous delivery of the nitric oxide along the flow path to the breathing tube.

28. The apparatus of claim 24, further comprising a sample line providing fluid communication between the one or more sensors and a location between the two or more electrodes and the breathing tube.

29. The apparatus of claim 28, wherein the one or more sensors are each arranged in the sample line and include a nitric oxide sensor, a nitrogen dioxide sensors, an oxygen sensor, a carbon dioxide sensor, and a pressure sensor.

30. The apparatus of claim 24, wherein the controller is further configured to detect inspiration based on feedback from at least one of the flow meter and the one or more sensors.

31. The apparatus of claim 30, wherein the controller is further configured to selectively supply an electrical signal to the power supply to initiate the one or more electric discharges after the onset of inspiration is detected and terminate the electrical signal before the end of inspiration.

32. The apparatus of claim 24, wherein the second layer is connected to a heat sink.

* * * * *